United States Patent [19]
Bennett et al.

[11] Patent Number: 6,015,894
[45] Date of Patent: *Jan. 18, 2000

[54] OLIGONUCLEOTIDE MODULATION OF CELL ADHESION

[75] Inventors: C. Frank Bennett, Carlsbad, Calif.; Christopher K. Mirabelli, Dover, Mass.

[73] Assignee: Isis Pharmaceuticals Inc., Carlsbad, Calif.

[*] Notice: This patent is subject to a terminal disclaimer.

[21] Appl. No.: 08/982,845

[22] Filed: Dec. 2, 1997

Related U.S. Application Data

[63] Continuation of application No. 08/440,740, May 12, 1995, Pat. No. 5,843,738, which is a continuation-in-part of application No. 08/063,167, May 17, 1993, Pat. No. 5,514,788, which is a continuation of application No. 07/969,151, Feb. 10, 1993, abandoned, which is a continuation-in-part of application No. 08/007,997, Jan. 21, 1993, Pat. No. 5,591,623, which is a continuation-in-part of application No. 07/939,855, Sep. 2, 1992, abandoned, which is a continuation-in-part of application No. 07/567,286, Aug. 14, 1990, abandoned.

[51] Int. Cl.$^7$ .................................................. C70H 21/00
[52] U.S. Cl. ........................................................ 536/24.5
[58] Field of Search ......................... 435/6, 375; 514/44; 536/24.31, 24.5

[56] References Cited

U.S. PATENT DOCUMENTS

| 5,514,788 | 5/1996 | Bennett et al. | 536/23.1 |
| 5,580,969 | 12/1996 | Hoke et al. | 536/24.5 |
| 5,591,623 | 1/1997 | Bennett et al. | 435/375 |

OTHER PUBLICATIONS

Adams et al., Intercellular Adhesion Molecule 1 on Liver Allografts During Rejection, *Lancet* 1989, 1122–1125.

Anderson and Springer, Leukocyte Adhesion Deficiency: An Inherited Defect in the Mac–1, LFA–1, and p150,95 Glycoproteins, *Ann. Rev. Med.* 1987, 38, 175–194.

Bevilacqua et al., Endothelial Leukocyte Adhesion Molecule 1: An Inducible Receptor for Neutorophils Related to Complement Regulatory Proteins and Lectins, *Science* 1989, 243, 1160–1165.

Bevilacqua et al., Identification of an Inducible Endothelial–leukocyte Adhesion Molecule, *Proc. Natl. Acad. Sci. USA* 1987, 84, 9238–9242.

Campbell et al., Intercellular Adhesion Molecule 1 is Induced on Isolated Endocrine Islet Cells by Cytokines but not be Reovirus Infection, *Proc. Natl. Acad. Sci. U.S.A.* 1989, 86, 4282–4286.

Cosimi et al., In vivo Effects of Monoclonal Antibody to ICAM–1 (CD54) in Nonhuman Primates with Renal Allografts, *J. Immunol.* 1990, 144, 4604–4612.

Dustin and Springer, Lymphocyte Function–associated Antigen–1 (LFA–1) Interaction with Intercellular Adhesion Molecule–1 (ICAM–1) is One of At Least Three Mechanisms for Lymphocye Adhesion to Cultured Endothelial Cells, *J. Cell Biol.* 1988, 107, 321–331.

Faull and Russ, Tubular Expression of Intercellular Adhesion Molecule–1 During Renal Allograft Rejection, *Transplantation* 1989, 48, 226–230.

Frohman et al., The induction of intercellular adhesion moleculte 1 (ICAM–1) expression on human fetal astrocytes by interferon–γ, tumor necrosis factor α, lymphotoxim, and interleukin–1: relevance to intracerebral antigen presentation, *J. Neuroimmunol.* 1989, 23, 117–124.

Greve et al., The Major Human Rhinovirus Receptor is ICAM–1, *Cell* 1989, 56, 839–847.

Griffiths and Nickoloff, Keratinocyte Intercellulr Adhesion Molecule–1 (ICAM–1) Expression Precedes Dermal T Lymphocytic Infiltratin in Allergic Contact Dermatitis (Rhus dermatitis), *Am. J. Pathology* 1989, 135, 1045–1053.

Hale et al., Immunohistologic Analysis of the Distribution of Cell Adhesion Molecules with the Inflammatory Synovial Microenvironment, *Arth. Rheum.* 1989, 32, 22–30.

Harlan, J.M., Leukocyte–Endothelial Interactions, *Blood* 1985, 65, 513–525.

Ho et al., Treatment of Severe Lichen Planus with Cyclosporing, *J. Am. Acad. Dermatol.* 1990, 22, 64–68.

Isobe et al., Specific Acceptance of Cardiac Allograft After Treatment with Antibodies to ICAM–1 and LFA–1, *Science* 1992, 255, 1125–1127.

Isobe et al., Early Detection of Rejection and Assessment of Cyclosporine Therapy by $^{111}$In Antimyosin Imagine in Mouse Heart Allografts, (1991) Circulation 84:1246–1255.

Lisby et al., Intercellular Adhesion Molecule–1 (ICAM–1) Expression Correlated to Inflammation, *Br. J. Dermatol.* 1989, 120, 479–484.

M. Zuker, On Findings All Suboptimal Foldings of an RNA Molecule, *Science* 1989, 244, 48–52.

(List continued on next page.)

*Primary Examiner*—David Guzo
*Assistant Examiner*—Thomas G. Larson
*Attorney, Agent, or Firm*—Law Offices of Jane Massey Licata

[57] ABSTRACT

Compositions and methods are provided for the treatment and diagnosis of diseases amenable to treatment through modulation of the synthesis or metabolism of intercellular adhesion molecules. In accordance with preferred embodiments, oligonucleotides are provided which are specifically hybridizable with nucleic acids encoding intercellular adhesion molecule-1, vascular cell adhesion molecule-1, and endothelial leukocyte adhesion molecule-1. The oligonucleotide comprises nucleotide units sufficient in identity and number to effect said specific hybridization. In other preferred embodiments, the oligonucleotides are specifically hybridizable with a transcription initiation site, a translation initiation site, 5'-untranslated sequences, 3'-untranslated sequences, and intervening sequences. Methods of treating animals suffering from disease amenable to therapeutic intervention by modulating cell adhesion proteins with an oligonucleotide specifically hybridizable with RNA or DNA corresponding to one of the foregoing proteins are disclosed. Methods for treatment of diseases responding to modulation cell adhesion molecules are disclosed.

4 Claims, 26 Drawing Sheets

OTHER PUBLICATIONS

Marlin et al., A soluble form of intercellular adhesion molecule–1 inhibits rhinovirus infection, *Nature* 1990, 344, 70–72.

Miller, D.E. and Welch, D.R., Cytokine Modulation of Intercellular Adhesion Molecule–1 Surface Expression on Human Melanoma Cells; Correlation with Adhesion of Peripheral Blook Leukocytes, (1990) Proc. Am. Assoc. Cancer Res. 13: 353.

Osborn et al., Direct Expression Cloning of Vascular Cell Adhesion Molecule 1, a Cytokine–Induced Endothelial Protein that Binds to Lymphocytes, *Cell* 1989 59:1203–11.

P.E. Nielsen, et al., Sequence–Selective Recognition of DNA by Strand Displacement with a Thymine–Substituted Polyamide, *Science* 1991, 254, 1497.

Petersheim, M. and D.H. Turner, Base–Stacking and Base––Pairing Contributions to Helix Stability: Thermodynamics of Double–Helix Formation with CCGG, CCGGp, CCGGAp, ACCGGp, CCGGUp, and ACCGGUp, *Biochemistry* 1983, 22, 256–263.

Rice and Bevilacqua, An Inducible Endothelial Cell Surface Glycoprotein Mediates Melanoma Adhesion, *Science* 1989, 246, 1303–1306.

Rice et al., Inducible Cell Adhesion Molecule 110 (INCAM–110) is an Endothelial Receptor for Lymphocytes, *J. Exp. Med.* 1990, 171, 1369–1374.

Rothenberg et al., Oligonucleotides as Anti–sense Inhibitors of Gene Expression: Therapeutic Implications, *J. Natl. Cancer Inst.* 1989, 81, 1539–1544.

Shiohara et al., Fixed Druge Eruption, *Arch. Dermatol.* 1989, 125, 1371–1376.

Staunton et al., A Cell Adhesion Molecule, ICAM–1, is the Major Surface Receptor for Rhimoviruses, *Cell* 1989, 56, 849–853.

Staunton et al., Primary Structure of ICAM–1 Demonstrates Interaction between Members of the Immunoglobulin and Integrin Supergene Families, *Cell* 1988, 52, 925–933.

Staunton et al., The Arrangement of the Immunoglobulin––like Domains of ICAM–1 and the Binding Sites for LFA–1 and Rhinovirus, *Cell* 1990, 61, 243–254.

Weetman et al., Expression of an Intercellular Ahdesion Molecule, ICAM–1, by Human Thyroid Cells, *J. Endocrinol.* 1989, 122, 185–191.

Wegner et al., Intercellular Adhesion Molecule–1 (ICAM–1) in the Phatogenesis of Asthma, *Science* 1990, 247, 456–459.

Wellicome et al., A Monoclonal Antibody that Detects a Novel Antigen on Endothelial Cells that is Induced by Tumor Necrosis Factor, IL–1, or Lipopolysaccharide, *J. Immunol.* 1990, 144, 2558–2565.

Zon, G., Oligonucleotide Analogues as Potential Chemotherapeutic Agents, *Pharmaceutical Res.* 1988, 5, 539–549.

Okayasu et al., A Novel Method in the Induction of Reliable Experimental Acute and Chronic Ulcerative Colitis in Mice, (1990) Gastroenterology 98:694–702.

Sambrook et al., *Molecular Cloning, A Laboratory Manual,* 2nd ed., Cold Spring Harbor Laboratory Press, 1989, vol. 2, p. 10.59.

FIG. 1A

```
GCTATAAGGA TCACGCGCCC CAGTCGACGC TGAGCTCCTC TGCTACTCAG AGTTGCAACC TCAGCCTCGCT

ATG GCT CCC AGC AGC CCC CGG CTG CCC GCA CTC GTC CTG TTC CCA
MET ALA PRO SER SER PRO ARG LEU PRO ALA LEU VAL LEU PHE PRO

GGA CCT AAT GCC CAG ACA TCT GTG TCC CCC CGG ATC GTC AAA GGC TCC GTG
GLY PRO ASN ALA GLN THR SER VAL SER PRO ARG ILE VAL LYS GLY SER VAL

CTG GTG ACA TGC AGC ACC TCC GAC CAG CCC AAG TTG TTG GGC ATA GAG CCG TTG CCT AAA
LEU VAL THR CYS SER THR SER ASP GLN PRO LYS LEU LEU GLY ILE GLU PRO LEU PRO LYS

AAG GAG TTG CTC CCT GGG AAC AAC CGG AAG CGG TAT GAA GTG CAA AAT GAA GAT AGC
LYS GLU LEU LEU PRO GLY ASN ASN ARG LYS ARG TYR GLU VAL GLN ASN GLU ASP SER

CAA CCA ATG TGC TAT TCA CAG CAG TCA ACA GCT AAA ACC TTC CTC ACC GTG TAC
GLN PRO MET CYS TYR SER GLN GLN SER THR ALA LYS THR PHE LEU THR VAL TYR

TGG ACT CCA GAA CGG GTG GAA CTG CCC TCT TGG CAG CCA GTG CAG AAG CTT ACC
TRP THR PRO GLU ARG VAL GLU LEU PRO SER TRP GLN PRO VAL GLN LYS LEU THR

CTA CGC TGC CAG GTG GAG GGT GCA CCC CGG GCC AAC CTC ACC GTG GTG CTC CGT GGG GAG
LEU ARG CYS GLN VAL GLU GLY ALA PRO ARG ALA ASN LEU THR VAL VAL LEU ARG GLY GLU

AAG GAG CTG AAA CGG AGC GAG GCA GTG GGG CCA GCT GTG ACG ACC ACG GTG CTG GTG AGG
LYS GLU LEU LYS ARG SER GLU ALA VAL GLY PRO ALA VAL THR THR THR VAL LEU VAL ARG

AGA GAT CAC CAT GGA GCC AAT TTC TCG TGC CGC ACT GAA CTG GAC CTG CGG CCC CAA GGG CTG GAG
ARG ASP HIS HIS GLY ALA ASN PHE SER CYS ARG THR GLU LEU ASP LEU ARG PRO GLN GLY LEU GLU
```

```
CTG TTT GAG AAC ACC TCG GCC CCC TAC CAG CTC CAG ACC TTT GTC CTG CCA GCG ACT CCC CCA CAA
LEU PHE GLU ASN THR SER ALA PRO TYR GLN LEU GLN THR PHE VAL LEU PRO ALA THR PRO PRO GLN

CTT GTC AGC CCC CGG CTA GTC GAG GTG GAC ACG GTC GTG TCC CTG GAC GGG CTG
LEU VAL SER PRO ARG LEU VAL GLU VAL ASP THR VAL VAL SER LEU ASP GLY LEU

TTC CCA GTC TCG GAG GCC CAG CAC GTC CTG GCA ACC GAC TTG AAC CCC ACA GTC ACC
PHE PRO VAL SER GLU ALA GLN HIS VAL LEU ALA THR ASP LEU ASN PRO THR VAL THR

TAT GGC AAC GAC TTC TCG GCC AAG CTG GCA GTG TCA GCC AGG CAG GAG GAC GGC ACC CAG
TYR GLY ASN ASP PHE SER ALA LYS LEU ALA VAL SER ALA ARG GLN GLU ASP GLY THR GLN

CGG CTG ACG TGT GCA GTA ATA CTG GGT GTC ACC GAG CAG ACA GAG ACA GTG ACC ATC TAC
ARG LEU THR CYS ALA VAL ILE LEU GLY VAL THR GLU GLN THR GLU THR VAL THR ILE TYR

AGC TTT CCG GCG CCC AAC GTG ATT CTG ATT CTG GGG ACC CAG GGG GTT CCA GCA GTG
SER PHE PRO ALA PRO ASN VAL ILE LEU ILE LEU GLY THR GLN GLY VAL PRO ALA THR VAL

AAG TGT GAG GCC CAC AGA GCC AAG GTG ACG ACA GAC AAC AAC GGG AAG ACC TTC TCT TGC TGC CCG
LYS CYS GLU ALA HIS ARG ALA LYS VAL THR THR ASP ASN ASN GLY LYS THR PHE SER CYS CYS ALA THR

AGG GCC CAG CTC CTG AAG CTG CAG CTT ATA CAC AAC AAG AAC CAG GGC GAG CGG CTT CGT GTC TAT GGC
ARG ALA GLN LEU LEU LYS LEU GLN LEU ILE HIS ASN LYS ASN GLN GLY GLU ARG LEU ARG VAL LEU GLY TYR

CTG GAG GTG GCC GGC GAT GAT TGT TCT CCG GGA ACA AAC TGG ACG AAC AAC AAT TCC CAG GTC TAT CCA ATG
LEU GLU VAL ALA GLY ASP ASP CYS SER PRO GLY THR ASN TRP THR ASN ASN ASN SER GLN VAL TYR GLY MET

CGA CTG GAC GAG GAG AGG GAT GAT TGT TGT CCC GGA AAC TGG ACG TTT CCA CCA GGA CTA GAG AAT GGC GCC ATG
ARG LEU ASP GLU GLU ARG ASP ASP CYS CYS PRO GLY ASN TRP THR PHE PRO PRO GLY LEU GLU ASN GLY ALA MET

TGC CAG GCT TGG GGG AAC CCA TTG CCC GAG CTA TGT TGT AAG CTA CTT AAG TGT CTA GCT GGC ATG CCA CTG CCC
CYS GLN ALA TRP GLY ASN PRO LEU PRO GLU LEU CYS CYS LYS LEU LEU LYS CYS LEU ALA GLY ASP THR PHE PRO LEU PRO
```

FIG. 1B

```
ATC GGG GAA TCA GTG ACT GTC ACT CGA GAT CTT GAG GGC ACC TAC CTC TGT CGG GCC AGG AGC ACT
ILE GLY GLU SER VAL THR VAL THR ARG ASP LEU GLU GLY THR TYR LEU CYS ARG ALA ARG SER THR

CAA GGG GAG GTC ACC CGC GAG ACC GTG AAT GTG CTC TCC CCC CGG TAT GAG ATT GTC ATC ATC
GLN GLY GLU VAL THR ARG GLU THR VAL ASN VAL LEU SER PRO ARG TYR GLU ILE VAL ILE ILE

ACT GTG GTA GCA GCC GCA GTC ATA ATG GGC ACT GCA GGC CTC TAT AAC CGC CAG
THR VAL VAL ALA ALA ALA VAL ILE MET GLY THR ALA GLY LEU SER TYR LEU TYR ASN ARG GLN

CGG AAG ATC AAG AAA TAC AGA CTA CAA CAG GCC CAA AAA GGG ACC CCC ATG AAA CCG AAC ACA CAA
ARG LYS ILE LYS LYS TYR ARG LEU GLN GLN ALA GLN LYS GLY THR PRO MET LYS PRO ASN THR GLN

GCC ACG CCT CCC TGA ACCTATCCCG GGACAGGGCC TCTTCCTCGG CCTTCCCATA TTGGTGGCAG TGGTGCCACA
ALA THR PRO PRO ***

CTGAACAGAG TGGAAGACAT ATGCCATGCA GCTACACCTA CCGGCCCTGG GACGCCGGAG GACAGGGCAT TGTCCTCAGT

CAGATACAAC AGCATTTGGG GCCATGGTAC CTGCACACCT AAAACACTAG GCCACGCATC TGATCTGTAG TCACATGACT

AAGCCAAGAG GAAGGAGCAA GACTCAAGAC ATGATTGATG TCTAGCCTGA TGAGAGGGGA AGTGGTGGGG

GAGACATAGC CCCACCATGA CTGGGAAATA CTGAAACTTG AAAACACAAA GGCCCACACT TCCTGACGGA TGCCAGCTTG

CTTACAGAAG AAGTGGCCCT CCATAGACAT GTGTAGCATC CCATGACAT TTTATTCATT TGTTATTTA CCAGCTATTT ATTGAGTGTC

GGCACTGCTG TCTACTGACC CCAACCCTTG ATGATATGTA TGCCCTCACG GAGCTCCCAG TCCATGTCAC ATTCAAGGTC ACCAGGTACA

TTTTATGTAG GCTAAATGAA CATAGGTCTC TGGCCTCACG GAGCTCCCAG TCCATGTCAC ATTCAAGGTC CCAACCTGCC

GTTGTACAGG TTGTACACTG CAGGAGAGTG CCTGGCAAAA AGATCAAATG GGGCTGGGAC TTCTCATTGG CCAACCTGCC

TTTCCCCAGA AGGAGTGATT TTTCTATCGG CACAAAAGCA CTATATGGAC TGTAATGTGT TCACAGGTTC AGAGATTACC
```

FIG. 1C

```
CAGTGAGGCC TTATTCCTCC CTTCCCCCCA AAACTGACAC CTTTGTTAGC CACCTCCCCA CCCACATACA TTTCTGCCAG
TGTTACAATG ACACTCAGCG GTCATGTCTG GACATGAGTG CCCAGGGAAT ATGCCCAAGC TATGCCTTGT CCTCTTGTCC
TGTTTGCATT TCACTGGGAG CTTGCACTAT TGCAGCTCCA GTTTCCTGCA GTGATCAGGG TCCTGCAAGC AGTGGGAAG
GGGCCAAGG TATTGGAGGA CTCCCTCCCA GCTTTGGAAG GGTCATCCGC GTGTGTGTGT GTGTGTATGT GTAGACAAGC
TCTCGCTCTG TCACCCAGGC TGGAGTGCAG TGGTGCAATC ATGGTTCACT GCAGTCTTGA CCTTTTGGGC TCAAGTGATC
CTCCCACCTC AGCCTCCTGA GTAGCTGGGA CCATAGGCTC ACAACACCAC ACCTGGCAAA TTTGATTTTT TTTTTTTTTT
TCAGAGACGG GGTCTCGCAA CATTGCCCAG ACTTCCTTTG TGTTAGTTAA TAAAGCTTTC TCAACTGCCA AAAAAAAAAA
AAAAAAA
```

```
TTCACATCAA AACTCCTATA CTGACCTGAG ACAGAGGCAG CAGTGATACC CACCTGAGAG ATCCTGTGTT TGA

ACAACTG CTTCCCAAAA CGGAAAGTAT TTCAAGCCTA AACCTTTGGG TGAAAGAAC TCTTGAAGTC ATG ATT
                                                                      met ile GCT TCA CAG TTT CTC TCA GCT CTC ACT TTG GTG CTT CTC ATT AAA GAG AGT GGA GCC TGG
ala ser gln phe leu ser ala leu thr leu val leu leu ile lys glu ser gly ala trp TCT TAC AAC ACC TCC ACG GAA GCT ATG ACT TAT GAT GAG AGT GCC AGT GCT TAT TGT CAG CAA
ser tyr asn thr ser thr glu ala met thr tyr asp glu ser ala ser tyr cys gln gln AGG TAC ACA CAC CTG GTT GCA ATT CAA AAC AAA GAA GAG ATT GAG ATC GLU TYR LEU AAC TCC ATA
arg tyr thr his leu val ala ile gln asn lys glu glu ile glu tyr leu asn ser ile TTG AGC TAT TCA CCA AGT TAT TAC TGG ATT GGA ATC AGA AAA GTC AAC AAT GTG TGG GTC
leu ser tyr ser pro ser tyr tyr trp ile gly ile arg lys val asn asn val trp val TGG GTA GGA ACC CAG AAA CCT CTG ACA GAA GAA GCC AAG AAC TGG GCT CCA GGT GAA CCC
trp val gly thr gln lys pro leu thr glu glu ala lys asn trp ala pro gly glu pro AAC AAT AGG CAA AAA GAT GAG GAG AGG TGC AGC AAG AAG CTT TAC ATC AAG CTT AAG AGA GAA AAA GAT GTG
asn asn arg gln lys asp glu glu arg cys ser lys lys leu tyr ile lys leu arg glu lys asp val GGC ATG TGG AAT GAT ACA TCC TGC TGC AGT CAC GGC CAC CTA GAG TGT GTA CGT GAT GCT GCC
gly met trp asn asp thr ser cys ser ser gly his gly his leu glu cys val glu thr ala ala TGT ACC AAT ACA TCC CCT GGC TTC AGT GGA CTC TTC GAA TGT GAG CAA ATT AAT TAC ACT
cys thr asn thr ser cys ser gly phe ser gly leu phe glu cys glu gln ile asn tyr thr TGC AAG TGT GAC CCT GGC TTC AGT GGA CTC TTC GAG CAA ATT GTG AAC TGT ACA GCC
cys lys cys asp pro gly phe ser gly leu phe cys glu gln ile val asn cys thr ala
```

```
CTG GAA TCC CCT GAG CAT GGA AGC CTG GTT TGC AGT CAC CCA CTG GGA AAC TTC AGC TAC
leu glu ser pro glu his gly ser leu val cys ser his pro leu gly asn phe ser tyr AAT TCT TCC TGC ATC AGC TGT GAT AGG GGT TAC CTG CCA AGC AGC ATG GAG ACC ATG
asn ser ser cys ser ile ser cys asp arg gly tyr leu pro ser ser met glu thr met CAG TGT ATG TCC TCT GGA GAA TCT GGA AGT GCT CCT ATT CCA GCC TGC AAT GTG GTT GAG TGT
gln cys met ser ser gly glu ser gly ser ala pro ile pro ala cys asn val val glu cys GAT GCT GTG ACA AAT CCA GCC TTC CAA TGT TTC GTG GAA TGT GGT TTC CAA AAC CCT GGA AGC TTC
asp ala val thr asn pro ala phe gln cys phe val glu cys gly phe gln asn pro gly ser phe CCA TGG ACA ACC TGT ACA TTT GAC TGT GAA GAA GGA TTT GAA CTA ATG GGA GCC CAG
pro trp thr thr cys thr phe asp cys glu glu gly phe glu leu met gly ala gln AGC CTT CAG TGT ACC TCA GGG AAT TGG GAC AAC GAG AAG CCA ACG TGT AAA GCT GTG
ser leu gln cys thr ser gly asn trp asp asn glu lys pro thr cys lys ala val ACA AGG GCC GTC CGC CAG CCT CAG AAT GGC TCT GTG AGG TGC AGC CAT TCC CCT GCT
thr arg ala val arg gln pro gln asn gly ser val arg cys ser his ser pro ala GGA GAG TTC ACC TTC AAA TCA TCC TGC AAC TTC ACC TGT GAG GAG GGG TTC ATG TTG CAG
gly glu phe thr phe lys ser ser cys asn phe thr cys glu glu gly phe met leu gln GGA CCA GCC CAG GTT GAA TGC ACT CAA GGG CAG TGG ACA CAG CAA ATC CCA GTT TGT
gly pro ala gln val glu cys thr gln gly gln trp thr gln gln ile pro val cys GAA GCT TTC CAG TGC ACA GCC TTG TCC AAC CCC GAG CGA GGC TAC ATG AAT TGT CTT CCT
glu ala phe gln cys thr ala leu ser asn pro glu arg gly tyr met asn cys leu pro
```

FIG. 2B

```
AGT GCT TCT GGC AGT TTC CGT TAT GGG TCC AGC TGT GAG TTC TCC TGT GAG CAG GGT TTT
ser ala ser gly ser phe arg tyr gly ser ser cys glu phe ser cys glu gln gly phe GTG TTG AAG GGA TCC AAA AGG CTC CAA TGT GGC GAG TTC GAC AAC GAG AAG
val leu lys gly ser lys arg leu gln cys gly glu phe asp asn glu lys CCC ACA TGT GAA GCT GTG AGA TGC GAT GCT GTC CAC CAG CCC AAG GGT GTG AGG
pro thr cys glu ala val arg cys asp ala val his gln pro lys gly val arg TGT GCT CAT TCC CCT ATT GGA GAA TTC ACC TAC AAG TAC TCC TTC AGC TGT GAG
cys ala his ser pro ile gly glu phe thr tyr lys tyr ser phe ser cys glu GAG GGA TTT GAA TTA TAT GGA TCA ACT CAA CTT GAG TGC ACA TCT CAG CAA TGG ACA
glu gly phe glu leu tyr gly ser thr gln leu glu cys thr ser gln gln trp thr GAA GTT CCT TCC TGC CAA GTG GTA AAA CTT CAA TGT GAG TGC TCA GCA GTT CCG GGA AAG ATC
glu val pro ser cys gln val val lys val lys cys glu cys ser ala val pro gly lys ile AAC ATG AGC TGC AGT GGG GAG GTG CCC GTG TTT GGC ACT GAG TGC AAG TTC GCC TGT CCT GAA
asn met ser cys ser gly glu val pro val phe gly thr glu cys lys phe ala cys pro glu GGA TGG ACG CTC AAT GGC TCT GCA GCT CCC ACT GAG TGT CGG ACA GGA CAC TGG ACA GAG TCT GGC
gly trp thr leu asn gly ser ala ala pro thr glu cys arg thr gly his trp thr glu ser gly CTA CCT ACC TGT GAA GCT CCC ACT GAG TCC AAC ATT CCC TTG GTA GCT GGA CTT TCT
leu pro thr cys glu ala pro thr glu ser asn ile pro leu val ala gly leu ser GCT GGA CTC TCC TCC ACA TTA GCA CCA TTT CTC CTC TGG CGG AAA TGC TTA
ala gly leu ser ser thr leu ala pro phe leu leu trp arg lys cys leu CGG AAA GCA AAA TTT GTT CCT GCC AGC TGC CAA AGC TGC CTT GAA CTT GAA TCA GAC GGA AGC
arg lys ala lys phe val pro ala ser cys gln ser cys leu glu leu glu ser asp gly ser
```

TAC CAA AAG CCT TCT TAC ATC CTT TAA GTTCAAA AGAATCAGAA ACAGGTGCAT CTGGGAACT A
tyr gln lys pro ser tyr ile leu ***

GAGGGATAC ACTGAAGTTA ACAGAGACAG ATAACTCTCC TCGGGTCTCT GGCCCTTCTT GCCTACTATG CCAG
ATGCCT TTATGGCTGA AACCGCAACA CCCATCACCA CTTCAATAGA TCAAAGTCCA GCAGGCAAGG ACGGCCT
TCA ACTGAAAAGA CTCAGTGTTC CCTTTCCTAC TCTCAGGATC AAGAAAGTGT TGGCTAATGA AGGGAAAGGA
TATTTCTTC CAAGCAAAGG TGAAGAGACC AAGACTCTGA AATCTCAGAA TTCCTTTTCT AACTCTCCCT TG
CTCGCTGT AAAATCTTGG CACAGAAACA CAATATTTTG TGGCTTTCTT TCTTTTGCCC TTCACAGTGT TTCGA
CAGCT GATTACACAG TTGCTGTGAT AAGAATGAAT AATAATTATC CAGAGTTTAG AGGAAAAAAA TGACTAAA
AA TATTATAACT TAAAAAAATG ACAGATGTTG AATGCCCACA GGCAAATGCA TGGAGGGTTG TTAATGGTGC
AAATCCTACT GAATGCTCTG TGCGAGGGTT ACTATGCACA ATTTAATCAC TTTCATCCCT ATGGGATTCA GTG
CTTCTTA AAGAGTTCTT AAGGATTGTG ATATTTTTAC TTGCATTGAA TATATTATAA TCTTCCATAC TTCTTC
ATTC AATACAAGTG TGGTAGGGAC TTAAAAAAACT TGTAAATGCT GTCAACTATG ATATGGTAAA AGTTACTTA
T TCTAGATTAC CCCCTCATTG TTTATTAACA AATTATGTTA CATCTGTTTT AAATTTATTT CAAAAGGGA A
ACTATTGTC CCCTAGCAAG GCATGATGTT AACCAGAATA AAGTTCCTGAG TGTTTTTACT ACAGTTGTTT TTTG
AAAACA TGGTAGAATT GGAGAGTAAA AACTGAATGG AAGGTTTGTA TATTGTCAGA TATTTTTCA GAAATAT
GTG GTTCCACGA TGAAAAACTT CCATGAGGCC AAACGTTTTG AACTAATAAA AGCATAAATG CAAACACACA
AAGGTATAT TTTATGAATG TCTTTGTTGG AAAAGAATAC AGAAAGATGG ATGTGCTTTG CATTCCTACA AA
GATGTTTG TCAGATGTGA TATGTAAACA TAATTCTTGT ATATTATTGA AGATTTTAAA TTCACAATAG AAACT

```
CACCA TGTAAAAGAG TCATCTGGTA GATTTTTAAC GAATGAAGAT GTCTAATAGT TATTCCCTAT TTGTTTTC
TT CTGTATGTTA GGGTGCTCTG GAAGAGAGGA ATGCCTGTGT GAGCAAGCAT TTATGTTTAT TTATAAGCAG
ATTAACAAT TCCAAAGGAA TCTCCAGTTT TCAGTTGATC ACTGGCAATG AAAAATTCTC AGTCAGTAAT TGC
CAAAGCT GCTCTAGCCT TGAGGAGTGT GAGAATCAAA ACTCTCCTAC ACTTCCATTA ACTTAGCATG TGTTGA
AAAA AAAAGTTTCA GAGAAGTTCT GGCTGAACAC TGGCAACGAC AAAGCCAACA GTCAAAACAG AGATGTGAT
A AGGATCAGAA CAGCAGAGGT TCTTTAAAG GGGCAGAAAA ACTCTGGGAA ATAAGAGAGA ACAACTACTG T
GATCAGGCT ATGTATGGAA TACAGTGTTA TTTTCTTTGA AATTGTTTAA GTGTTGTAAA TATTTATGTA AACT
GCATTA GAAATTAGCT GTGTGAAATA CCAGTGTGGT TTGTGTTTGA GTTTTATTGA GAATTTTAAA TTATAAC
TTA AAATATTTTA TAATTTTTAA AGTATATATT TATTTAAGCT TATGTCAGAC CTATTTGACA TAACACTATA
AAGGTTGACA ATAAATGTGC TTATGTTT
```

CGGGCCTCAC TGGCTTCAGG AGCTGAATAC CCTCCCAGGC ACACACAGGT GGGACACAAA TAAGGGTTTT GGA
ACCACTA TTTTCTCATC ACGACAGCAA CTTAAA ATG CCT GGG AAG ATG GTC CTT GGA GCC
                                          met pro gly lys met val val ile leu gly ala TCA AAT ATA CTT TGG ATA ATG TTT GCA GCT TCT CAA GCT TTT AAA ATC GAG ACC ACC CCA
ser asn ile leu trp ile met phe ala ala ser gln ala phe lys ile glu thr thr pro GAA TCT AGA TAT CTT GCT CAG ATT GGT GAC CTC TCA TTG ACT TGC AGC ACC ACA GGC
glu ser arg tyr leu ala gln ile gly asp ser val ser leu thr cys ser thr thr gly TGT GAG TCC CCA TTT TTC TGG AGA ACC CAG ATA GAT AGT CCA CTG AAT GGG AAG GTG
cys glu ser pro phe phe trp arg thr gln ile asp ser pro leu asn gly lys val ACG AAT GAG GGG ACC ACA TCT ACG CTG ACA ATG AAT CCT GTT AGT TTT GGG AAC GAA CAC
thr asn glu gly thr thr ser thr leu thr met asn pro val ser phe gly asn glu his TCT TAC CTG TGC ACA GCA ACT TGT GAA TCT AGG AAA TTG GAA TTG AAA GGA ATC CAG GTG GAG
ser tyr leu cys thr ala thr cys glu ser arg lys leu glu lys gly ile gln val glu ATC TAC TCT TTT CCT AAG GAT ATT CAT TTG AGT GGC CCT CTG GAG GCT CTG GGG AAG
ile tyr ser phe pro lys asp ile his leu ser gly pro leu glu ala gly lys CCG ATC ACA GTC AAG TGT TCA GTT GCT GAT GTA TAC CCA TTT GAC AGG CTG GAG ATA GAC
pro ile thr val lys cys ser val ala asp val tyr pro phe asp arg leu glu ile asp TTA CTG AAA GGA GAT CAT CTC ATG AAG CTC ATG AAG TTT CTG GAG GAT GCA GAC AGG AAG
leu leu lys gly asp his leu met lys ser gln glu phe leu glu asp ala asp arg lys TCC CTG GAA ACC AAG AGT TTG GAA GTA ACC TTT ACT CCT GTC ATT GAT ATT GGA AAA
ser leu glu thr lys ser leu glu val thr phe thr pro val ile glu asp ile gly lys GTT CTT GTT TGC CGA GCT TTA CAC ATT GAT GAA ATG GAT TCT CCC ACA GTA AGG
val leu val cys arg ala lys leu his ile asp glu met asp ser val pro thr val arg CAG GCT GTA AAA GAA TTG CAA GTC TAC ATA TCA CCC AAG AAT ACA GTT ATT TCT GTG AAT
gln ala val lys glu leu gln val tyr ile ser pro lys asn thr val ile ser val asn CCA TCC ACA AAG CTG CAA GGT GAA GGT GGC TCT GTG ACC TGT TCC AGC GAG GGT CTA
pro ser thr lys leu gln glu gly gly ser val thr cys ser ser glu gly leu CCA GCT CCA GAG ATT TTC TGG AGT AAG AAA TTA GAT AAT GGG CTA CAG CAC CTT TCT
pro ala pro glu ile phe trp ser lys lys leu asp asn gly leu gln his leu ser GGA AAT GCA ACT CTC ACC TTA ATT GCT ATG AGG GAA GAT TCT GGA ATT CAA TAT GTG TGT
gly asn ala thr leu ile ala met arg glu asp ser gly ile gln tyr val cys GAA GGA GTT AAT TTG ATT GGG AAA AAC AGA AGT ATG GAG GTG GAA TTA GTT GTT CAA GCA TTC
glu gly val asn leu ile gly lys asn arg ser met glu val glu leu val gln ala phe CCT AGA GAT CCA ATC GAG ATG GGT GGC CTC GTG AAT GGG TCT ACT GTA
pro arg asp pro ile glu met ser gly gly leu val asn gly ser val thr val AGC TGC AAG GTT CCT AGC GTG TAC CCC CTT GAC CGG ATT GAA CTT GAA AAG GGG
ser cys lys val pro ser val tyr pro leu asp arg ile glu leu lys gly GAG ACT ATT CTG GAG AAT ATA GAG TTT TTG GAG GAT ACG GAT ATG AAA TCT CTA GAG AAC
glu thr ile leu glu asn ile glu phe leu glu asp thr asp met lys ser leu glu asn AAA AGT TTG GAA ATG ACC TTC ATC CCT ACC ATT GAA GAT ACT GGA AAA GCT CTT GTT TGT
lys ser leu glu met thr phe ile pro thr ile glu asp thr gly lys ala leu val cys CAG GCT TTA CAT CAT ATT GAT GAC ATG GAA TTC GAA CCC AAA CAA AGG CAG AGT ACG CAA
gln ala leu his his ile asp asp met glu phe glu pro lys gln arg gln ser thr gln ACA CTT TAT GTC AAT GTT GCC CCC AGA GAT ACA ACC GTC TTG GTC AGC CCT TCC TCC ATC
thr leu tyr val asn val ala pro arg asp thr thr val leu val ser pro ser ile CTG GAG GAA GGC AGT TCT GTG AAT ATG ACA TGC TTG AGC CAG GGC TTT CCT GCT CCG AAA
leu glu glu gly ser ser val asn met thr cys leu ser gln gly phe pro ala pro lys

FIG. 3B

```
ATC CTG TGG AGC AGG CAG CTC CCT AAC GGG GAG CTA CAG CCT CTT TCT GAG AAT GCA ACT
ile leu trp ser arg gln leu pro asn gly glu leu gln pro leu ser glu asn ala thr CTC ACC TTA ATT TCT ACA AAA ATG GAA GAT TCT GGG GTT TAT TTA TGT GAA GGA ATT AAC
leu thr leu ile ser thr lys met glu asp ser gly val tyr leu cys glu gly ile asn CAG GCT GGA AGA AGC AGA AAG GAA AAG GTG GAA TTA ATT ATC CAA GTT ACT CCA AAA GAC ATA
gln ala gly arg ser arg lys glu lys val glu leu ile ile gln val thr pro lys asp ile AAA CTT ACA GCT TTT CCT TCT GAG AGT GTC AAA GAA GGA GAC AAA GAC GTC ATC ATC TCT TGT
lys leu thr ala phe pro ser glu ser val lys glu gly asp lys asp val ile ile ser cys ACA TGT GGA AAT GTT CCA GAA ACA ATC TGG ATA ATC CTG AAG AAA AAG CTG GAG ACA GGA GAC
thr cys gly asn val pro glu thr ile trp ile ile leu lys lys lys leu glu thr gly asp ACA GTA CTA AAA TCT ATA GAT GGC GCC TAT GCC ATC CGA ATC GGC TCA CAA TTA AGA AGT TTA ACA CTT
thr val leu lys ser ile asp gly ala tyr ala ile arg ile gly ser gln leu arg ser leu thr leu GGA GTA TAT GAA TGT GAA GCA GAA AAC AAA GAC TAT TTT TCT CCT GAG CTT CTC GTG CTC TAT
gly val tyr glu cys glu ala glu asn lys asp tyr phe ser pro glu leu leu val leu tyr GAT GTT CAA GGA AGA GAA AAC AAA AAC GCC ATT GGA ATG ATT TAC TTT GCA AGA AAA GCC
asp val gln gly arg glu asn lys asn ala ile gly met ile tyr phe ala arg lys ala TTT GCA TCC TCC TTA ATA ATA CCT GCC ATT GGA ATG ATT TAC TTT GCA AGA AAA GCC
phe ala ser ser leu ile ile pro ala ile gly met ile tyr phe ala arg lys ala AAC ATG AAG GGG TCA TAT AGT CTT GTA GAA GCA CAG AAA TCA AAA GTG TAG CTAATGCTTG
asn met lys gly ser tyr ser leu val glu ala gln lys ser lys val ***

ATATGTTCAA CTGGAGACAC TATTTATCTG TGCAAATCCT TGATACTGCT CATCATTCCT TGAGAAAAAC AAT

GAGCTGA GAGGCAGACT TCCCTGAATG TATTGAACTT GGAAAGAAAT GCCCATCTAT GTCCCTTGCT GTGAGC

AAGA AGTCAAAGTA AAACTTGCTG CCTGAAGAAC AGTAACTGCC ATCAAGATGA GAGAACTGGA GGAGTCCT

T GATCTGTATA TACAATAACA TAATTTGTAC ATATGTAAAA TAAAATTATG CCATAGCAAG ATTGCTTAAAA
```

FIG. 3C

```
TAGCAACAC TCTATATTTA GATTGTTAAA ATAACTAGTG TTGCTTGGAC TATTATAATT TAATGCATGT TAGG
AAAATT TCACATTAAT ATTTGCTGAC AGCTGACCTT TGTCATCTTT CTTCTATTTT ATTCCCTTTC ACAAAAT
TTT ATTCCTATAT AGTTTATTGA CAATAATTTC AGTTTTGTA AAGATGCCGG GTTTTATATT TTTATAGACA
AATAATAAGC AAAGGGAGCA CTGGGTTGAC TTTCAGGTAC TAAATACCTC AACCTATGGT ATAATGGTTG AC
TGGGTTTC TCTGTATAGT ACTGGCATGG TACGGAGATG TTTCACGAAG TTTGTTCATC AGACTCCTGT GCAAC
TTTCC CAATGTGGCC TAAAAATGCA ACTTCTTTTT ATTTTCTTTT GTAAATGTTT AGTTTTTTT GTATAGTA
AA GTGATAAATTT CTGGAATTAA AAA
```

FIG. 3D

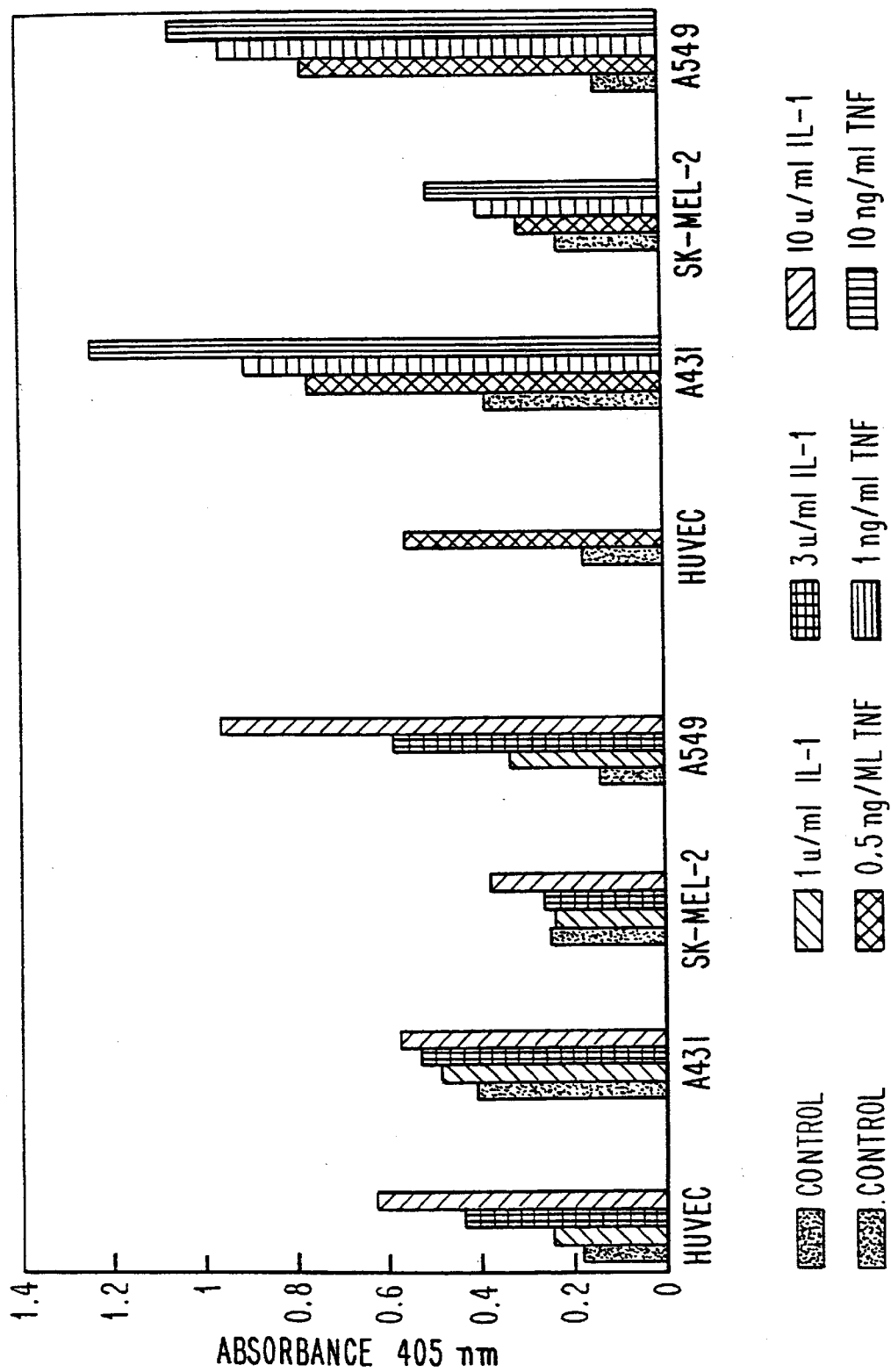

SEQUENCE LISTING (1) GENERAL INFORMATION:

(iii) NUMBER OF SEQUENCES: 87

(2) INFORMATION FOR SEQ ID NO:1:

(i) SEQUENCE CHARACTERISTICS:
           (A) LENGTH: 18
           (B) TYPE: Nucleic Acid
           (C) STRANDEDNESS: Single
           (D) TOPOLOGY: Linear (iv) ANTI-SENSE: Yes (xi) SEQUENCE DESCRIPTION:  SEQ ID NO: 1:

TGGGAGCCAT AGCGAGGC                                               18

(2) INFORMATION FOR SEQ ID NO: 2:

(i) SEQUENCE CHARACTERISTICS:
           (A) LENGTH: 20
           (B) TYPE: Nucleic Acid
           (C) STRANDEDNESS: Single
           (D) TOPOLOGY: Linear (iv) ANTI-SENSE: Yes (xi) SEQUENCE DESCRIPTION:  SEQ ID NO: 2:

GAGGAGCTCA GCGTCGACTG                                             20

(2) INFORMATION FOR SEQ ID NO: 3:

(i) SEQUENCE CHARACTERISTICS:
           (A) LENGTH: 21
           (B) TYPE: Nucleic Acid
           (C) STRANDEDNESS: Single
           (D) TOPOLOGY: Linear (iv) ANTI-SENSE: Yes (xi) SEQUENCE DESCRIPTION:  SEQ ID NO: 3:

GACACTCAAT AAATAGCTGG T                                           21

(2) INFORMATION FOR SEQ ID NO: 4:

(i) SEQUENCE CHARACTERISTICS:
           (A) LENGTH: 18
           (B) TYPE: Nucleic Acid
           (C) STRANDEDNESS: Single
           (D) TOPOLOGY: Linear (iv) ANTI-SENSE: Yes (xi) SEQUENCE DESCRIPTION:  SEQ ID NO: 4:

GAGGCTGAGG TGGGAGGA                                               18

(2) INFORMATION FOR SEQ ID NO: 5:

(i) SEQUENCE CHARACTERISTICS:
           (A) LENGTH: 18
           (B) TYPE: Nucleic Acid
           (C) STRANDEDNESS: Single
           (D) TOPOLOGY: Linear (iv) ANTI-SENSE: Yes (xi) SEQUENCE DESCRIPTION:  SEQ ID NO: 5:

```
CGATGGGCAG TGGGAAAG                                                    18

(2) INFORMATION FOR SEQ ID NO: 6:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 6:

GGGCGCGTGA TCCTTATAGC                                                  20

(2) INFORMATION FOR SEQ ID NO: 7:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 7:

CATAGCGAGG CTGAGGTTGC                                                  20

(2) INFORMATION FOR SEQ ID NO: 8:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 8:

CGGGGGCTGC TGGGAGCCAT                                                  20

(2) INFORMATION FOR SEQ ID NO: 9:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 9:

AGAGCCCCGA GCAGGACCAG                                                  20

(2) INFORMATION FOR SEQ ID NO: 10:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 10:

TGCCCATCAG GGCAGTTTGA                                                  20

(2) INFORMATION FOR SEQ ID NO: 11:
```

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 11:

GGTCACACTG ACTGAGGCCT                                                    20

(2) INFORMATION FOR SEQ ID NO: 12:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 12:

CTCGCGGGTG ACCTCCCCTT                                                    20

(2) INFORMATION FOR SEQ ID NO: 13:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 13:

TCAGGGAGGC GTGGCTTGTG                                                    20

(2) INFORMATION FOR SEQ ID NO: 14:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 14:

CCTGTCCCGG GATAGGTTC A                                                   20

(2) INFORMATION FOR SEQ ID NO: 15:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 15:

CCCCCACCAC TTCCCCTCTC                                                    20

(2) INFORMATION FOR SEQ ID NO: 16:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 16:

TTGAGAAAGC TTTATTAACT                                                     20

(2) INFORMATION FOR SEQ ID NO: 17:

(i) SEQUENCE CHARACTERISTICS:
            (A) LENGTH: 14
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 17:

AGCCATAGCG AGGC                                                           14

(2) INFORMATION FOR SEQ ID NO: 18:

(i) SEQUENCE CHARACTERISTICS:
            (A) LENGTH: 12
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 18:

CCATAGCGAG GC                                                             12

(2) INFORMATION FOR SEQ ID NO: 19:

(i) SEQUENCE CHARACTERISTICS:
            (A) LENGTH: 10
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 19:

ATAGCGAGGC                                                                10

(2) INFORMATION FOR SEQ ID NO: 20:

(i) SEQUENCE CHARACTERISTICS:
            (A) LENGTH: 16
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 20:

TGGGAGCCAT AGCGAG                                                         16

(2) INFORMATION FOR SEQ ID NO: 21:

(i) SEQUENCE CHARACTERISTICS:
            (A) LENGTH: 16
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 21:

GGAGCCATAG CGAGGC                                                          16

(2) INFORMATION FOR SEQ ID NO: 22:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 22:

GCCCAAGCTG GCATCCGTCA                                                      20

(2) INFORMATION FOR SEQ ID NO: 23:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 23:

TCTGTAAGTC TGTGGGCCTC                                                      20

(2) INFORMATION FOR SEQ ID NO: 24:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 24:

AGTCTTGCTC CTTCCTCTTG                                                      20

(2) INFORMATION FOR SEQ ID NO: 25:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 25:

CTCATCAGGC TAGACTTTAA                                                      20

(2) INFORMATION FOR SEQ ID NO: 26:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 26:

TGTCCTCATG GTGGGGCTAT                                                      20

(2) INFORMATION FOR SEQ ID NO: 27:

(i) SEQUENCE CHARACTERISTICS:
        (A) LENGTH: 22
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 27:

TCTGAGTAGC AGAGGAGCTC GA                                              22

(2) INFORMATION FOR SEQ ID NO: 28:

(i) SEQUENCE CHARACTERISTICS:
        (A) LENGTH: 22
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 28:

CAATCATGAC TTCAAGAGTT CT                                              22

(2) INFORMATION FOR SEQ ID NO: 29:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 29:

ACCACACTGG TATTTCACAC                                                 20

(2) INFORMATION FOR SEQ ID NO: 30:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 30:

GTATGGAAGA TTATAATATA T                                               21

(2) INFORMATION FOR SEQ ID NO: 31:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 31:

CACAATCCTT AAGAACTCTT T                                               21

(2) INFORMATION FOR SEQ ID NO: 32:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 32:

ACCTCTGCTG TTCTGATCCT                                                                            20

(2) INFORMATION FOR SEQ ID NO: 33:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 33:

CTGCTGCCTC TGTCTCAGGT                                                                            20

(2) INFORMATION FOR SEQ ID NO: 34:

(i) SEQUENCE CHARACTERISTICS:
        (A) LENGTH: 15
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 34:

GGTATTTGAC ACAGC                                                                                 15

(2) INFORMATION FOR SEQ ID NO: 35:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 35:

AATCATGACT TCAAGAGTTC T                                                                          21

(2) INFORMATION FOR SEQ ID NO: 36:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 36:

TGAAGCAATC ATGACTTCAA G                                                                          21

(2) INFORMATION FOR SEQ ID NO: 37:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 37:

```
TATAGGAGTT TTGATGTGAA                                      20

(2) INFORMATION FOR SEQ ID NO: 38:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 38:

ACAATGAGGG GGTAATCTAC A                                    21

(2) INFORMATION FOR SEQ ID NO: 39:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 39:

GACAATATAC AAACCTTCCA T                                    21

(2) INFORMATION FOR SEQ ID NO: 40:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 40:

CCAGGCATTT TAAGTTGCTG T                                    21

(2) INFORMATION FOR SEQ ID NO: 41:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 41:

CCTGAAGCCA GTGAGGCCCG                                      20

(2) INFORMATION FOR SEQ ID NO: 42:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 42:

GATGAGAAAA TAGTGGAACC A                                    21

(2) INFORMATION FOR SEQ ID NO: 43:
```

(i) SEQUENCE CHARACTERISTICS:
            (A) LENGTH: 19
            (B) TYPE: Nucleic Acid
            (C) STRANDEDNESS: Single
            (D) TOPOLOGY: Linear (iv) ANTI-SENSE: Yes (xi) SEQUENCE DESCRIPTION:  SEQ ID NO: 43:

CTGAGCAAGA TATCTAGAT                                                    19

(2) INFORMATION FOR SEQ ID NO: 44:

(i) SEQUENCE CHARACTERISTICS:
            (A) LENGTH: 19
            (B) TYPE: Nucleic Acid
            (C) STRANDEDNESS: Single
            (D) TOPOLOGY: Linear (iv) ANTI-SENSE: Yes (xi) SEQUENCE DESCRIPTION:  SEQ ID NO: 44:

CTACACTTTT GATTTCTGT                                                    19

(2) INFORMATION FOR SEQ ID NO: 45:

(i) SEQUENCE CHARACTERISTICS:
            (A) LENGTH: 22
            (B) TYPE: Nucleic Acid
            (C) STRANDEDNESS: Single
            (D) TOPOLOGY: Linear (iv) ANTI-SENSE: Yes (xi) SEQUENCE DESCRIPTION:  SEQ ID NO: 45:

TTGAACATAT CAAGCATTAG CT                                                22

(2) INFORMATION FOR SEQ ID NO: 46:

(i) SEQUENCE CHARACTERISTICS:
            (A) LENGTH: 22
            (B) TYPE: Nucleic Acid
            (C) STRANDEDNESS: Single
            (D) TOPOLOGY: Linear (iv) ANTI-SENSE: Yes (xi) SEQUENCE DESCRIPTION:  SEQ ID NO: 46:

TTTACATATG TACAAATTAT GT                                                22

(2) INFORMATION FOR SEQ ID NO: 47:

(i) SEQUENCE CHARACTERISTICS:
            (A) LENGTH: 22
            (B) TYPE: Nucleic Acid
            (C) STRANDEDNESS: Single
            (D) TOPOLOGY: Linear (iv) ANTI-SENSE: Yes (xi) SEQUENCE DESCRIPTION:  SEQ ID NO: 47:

AATTATCACT TTACTATACA AA                                                22

(2) INFORMATION FOR SEQ ID NO: 48:

(i) SEQUENCE CHARACTERISTICS:
            (A) LENGTH: 21
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 48:

AGGGCTGACC AAGACGGTTG T                                    21

(2) INFORMATION FOR SEQ ID NO: 49:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 49:

CCATCTTCCC AGGCATTTTA                                      20

(2) INFORMATION FOR SEQ ID NO: 50:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 50:

AACCCAGTGC TCCCTTTGCT                                      20

(2) INFORMATION FOR SEQ ID NO: 51:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 51:

GGCCACATTG GGAAAGTTGC                                      20

(2) INFORMATION FOR SEQ ID NO: 52:

(i) SEQUENCE CHARACTERISTICS:
        (A) LENGTH:  20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 52:

GAAGTCAGCC AAGAACAGCT                                      20

(2) INFORMATION FOR SEQ ID NO:  53:

(i) SEQUENCE CHARACTERISTICS:
        (A) LENGTH:  20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 53:

ACAGGATCTC TCAGGTGGGT                                          20

(2) INFORMATION FOR SEQ ID NO: 54:

(i) SEQUENCE CHARACTERISTICS:
        (A) LENGTH:  20
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 54:

CCAAAGTGAG AGCTGAGAGA                                          20

(2) INFORMATION FOR SEQ ID NO: 55:

(i) SEQUENCE CHARACTERISTICS:
        (A) LENGTH:  20
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 55:

CTGATTCAAG GCTTTGGCAG                                          20

(2) INFORMATION FOR SEQ ID NO: 56:

(i) SEQUENCE CHARACTERISTICS:
        (A) LENGTH:  20
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 56:

TTCCCCAGAT GCACCTGTTT                                          20

(2) INFORMATION FOR SEQ ID NO: 57:

(i) SEQUENCE CHARACTERISTICS:
        (A) LENGTH:  20
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 57:

GGGCCAGAGA CCCGAGGAGA                                          20

(2) INFORMATION FOR SEQ ID NO: 58:

(i) SEQUENCE CHARACTERISTICS:
        (A) LENGTH:  20
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 58:

ACGTTTGGCC TCATGGAAGT                                          20

(2) INFORMATION FOR SEQ ID NO: 59:

(i) SEQUENCE CHARACTERISTICS:
            (A) LENGTH:  20
            (B) TYPE: Nucleic Acid
            (C) STRANDEDNESS: Single
            (D) TOPOLOGY: Linear (iv) ANTI-SENSE: Yes (xi) SEQUENCE DESCRIPTION:  SEQ ID NO: 59:

GGAATGCAAA GCACATCCAT                                                  20

(2) INFORMATION FOR SEQ ID NO: 60:

(i) SEQUENCE CHARACTERISTICS:
            (A) LENGTH:  20
            (B) TYPE: Nucleic Acid
            (C) STRANDEDNESS: Single
            (D) TOPOLOGY: Linear (iv) ANTI-SENSE: Yes (xi) SEQUENCE DESCRIPTION:  SEQ ID NO: 60:

CGATGCAGAT ACCGCGGAGT                                                  20

(2) INFORMATION FOR SEQ ID NO: 61:

(i) SEQUENCE CHARACTERISTICS:
            (A) LENGTH:  20
            (B) TYPE: Nucleic Acid
            (C) STRANDEDNESS: Single
            (D) TOPOLOGY: Linear (iv) ANTI-SENSE: Yes (xi) SEQUENCE DESCRIPTION:  SEQ ID NO: 61:

GCCTGGGAGG GTATTCAGCT                                                  20

(2) INFORMATION FOR SEQ ID NO: 62:

(i) SEQUENCE CHARACTERISTICS:
            (A) LENGTH:  20
            (B) TYPE: Nucleic Acid
            (C) STRANDEDNESS: Single
            (D) TOPOLOGY: Linear (iv) ANTI-SENSE: Yes (xi) SEQUENCE DESCRIPTION:  SEQ ID NO: 62:

CCTGTGTGTG CCTGGGAGGG                                                  20

(2) INFORMATION FOR SEQ ID NO: 63:

(i) SEQUENCE CHARACTERISTICS:
            (A) LENGTH:  20
            (B) TYPE: Nucleic Acid
            (C) STRANDEDNESS: Single
            (D) TOPOLOGY: Linear (iv) ANTI-SENSE: Yes (xi) SEQUENCE DESCRIPTION:  SEQ ID NO: 63:

GGCATTTTAA GTTGCTGTCG                                                  20

(2) INFORMATION FOR SEQ ID NO: 64:

(i) SEQUENCE CHARACTERISTICS:
            (A) LENGTH:  20
            (B) TYPE: Nucleic Acid
            (C) STRANDEDNESS: Single
            (D) TOPOLOGY: Linear (iv) ANTI-SENSE: Yes (xi) SEQUENCE DESCRIPTION: SEQ ID NO: 64:

CAGCCTGCCT TACTGTGGGC                                            20

(2) INFORMATION FOR SEQ ID NO: 65:

(i) SEQUENCE CHARACTERISTICS:
              (A) LENGTH:   21
              (B) TYPE: Nucleic Acid
              (C) STRANDEDNESS: Single
              (D) TOPOLOGY: Linear (iv) ANTI-SENSE: Yes (xi) SEQUENCE DESCRIPTION: SEQ ID NO: 65:

CTTGAACAAT TAATTCCACC T                                          21

(2) INFORMATION FOR SEQ ID NO: 66:

(i) SEQUENCE CHARACTERISTICS:
              (A) LENGTH:   21
              (B) TYPE: Nucleic Acid
              (C) STRANDEDNESS: Single
              (D) TOPOLOGY: Linear (iv) ANTI-SENSE: Yes (xi) SEQUENCE DESCRIPTION: SEQ ID NO: 66:

TTACCATTGA CATAAAGTGT T                                          21

(2) INFORMATION FOR SEQ ID NO: 67:

(i) SEQUENCE CHARACTERISTICS:
              (A) LENGTH:   20
              (B) TYPE: Nucleic Acid
              (C) STRANDEDNESS: Single
              (D) TOPOLOGY: Linear (iv) ANTI-SENSE: Yes (xi) SEQUENCE DESCRIPTION: SEQ ID NO: 67:

CTGTGTCTCC TGTCTCCGCT                                            20

(2) INFORMATION FOR SEQ ID NO: 68:

(i) SEQUENCE CHARACTERISTICS:
              (A) LENGTH:   21
              (B) TYPE: Nucleic Acid
              (C) STRANDEDNESS: Single
              (D) TOPOLOGY: Linear (iv) ANTI-SENSE: Yes (xi) SEQUENCE DESCRIPTION: SEQ ID NO: 68:

GTCTTTGTTG TTTTCTCTTC C                                          21

(2) INFORMATION FOR SEQ ID NO: 69:

(i) SEQUENCE CHARACTERISTICS:
              (A) LENGTH:   20
              (B) TYPE: Nucleic Acid
              (C) STRANDEDNESS: Single
              (D) TOPOLOGY: Linear (iv) ANTI-SENSE: Yes (xi) SEQUENCE DESCRIPTION: SEQ ID NO: 69:

TGAACATATC AAGCATTAGC                                           20

(2) INFORMATION FOR SEQ ID NO: 70:

(i) SEQUENCE CHARACTERISTICS:
        (A) LENGTH:   20
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 70:

GCAATCTTGC TATGGCATAA                                           20

(2) INFORMATION FOR SEQ ID NO: 71:

(i) SEQUENCE CHARACTERISTICS:
        (A) LENGTH:   20
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 71:

CCCGGCATCT TTACAAAACC                                           20

(2) INFORMATION FOR SEQ ID NO: 72:

(i) SEQUENCE CHARACTERISTICS:
        (A) LENGTH:   20
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 72:

AACATCTCCG TACCATGCCA                                           20

(2) INFORMATION FOR SEQ ID NO: 73:

(i) SEQUENCE CHARACTERISTICS:
        (A) LENGTH:   22
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 73:

TCACTGCTGC CTCTGTCTCA GG                                        22

(2) INFORMATION FOR SEQ ID NO: 74:

(i) SEQUENCE CHARACTERISTICS:
        (A) LENGTH: 23
        (B) TYPE: Nucleic Acid
        (C) STRANDEDNESS: Single
        (D) TOPOLOGY: Linear (iv) ANTI-SENSE: Yes (xi) SEQUENCE DESCRIPTION:  SEQ ID NO: 74:

TGATTCTTTT GAACTTAAAA GGA                                       23

(2) INFORMATION FOR SEQ ID NO: 75:

```
     (i) SEQUENCE CHARACTERISTICS:
         (A) LENGTH: 20
         (B) TYPE: Nucleic Acid
         (C) STRANDEDNESS: Single
         (D) TOPOLOGY: Linear (iv) ANTI-SENSE: Yes (xi) SEQUENCE DESCRIPTION: SEQ ID NO: 75:

TTAAAGGATG TAAGAAGGCT                                                    20

(2) INFORMATION FOR SEQ ID NO: 76:

(i) SEQUENCE CHARACTERISTICS:
         (A) LENGTH: 19
         (B) TYPE: Nucleic Acid
         (C) STRANDEDNESS: Single
         (D) TOPOLOGY: Linear (iv) ANTI-SENSE: Yes (xi) SEQUENCE DESCRIPTION: SEQ ID NO: 76:

CATAAGCACA TTTATTGTC                                                     19

(2) INFORMATION FOR SEQ ID NO: 77:

(i) SEQUENCE CHARACTERISTICS:
         (A) LENGTH: 20
         (B) TYPE: Nucleic Acid
         (C) STRANDEDNESS: Single
         (D) TOPOLOGY: Linear (iv) ANTI-SENSE: Yes (xi) SEQUENCE DESCRIPTION: SEQ ID NO: 77:

TTTTGGGAAG CAGTTGTTCA                                                    20

(2) INFORMATION FOR SEQ ID NO: 78:

(i) SEQUENCE CHARACTERISTICS:
         (A) LENGTH: 21
         (B) TYPE: Nucleic Acid
         (C) STRANDEDNESS: Single
         (D) TOPOLOGY: Linear (iv) ANTI-SENSE: Yes (xi) SEQUENCE DESCRIPTION: SEQ ID NO: 78:

AACTGTGAAG CAATCATGAC T                                                  21

(2) INFORMATION FOR SEQ ID NO: 79:

(i) SEQUENCE CHARACTERISTICS:
         (A) LENGTH: 22
         (B) TYPE: Nucleic Acid
         (C) STRANDEDNESS: Single
         (D) TOPOLOGY: Linear (iv) ANTI-SENSE: Yes (xi) SEQUENCE DESCRIPTION: SEQ ID NO: 79:

CCTTGAGTGG TGCATTCAAC CT                                                 22

(2) INFORMATION FOR SEQ ID NO: 80:

(i) SEQUENCE CHARACTERISTICS:
         (A) LENGTH: 22
         (B) TYPE: Nucleic Acid
         (C) STRANDEDNESS: Single
         (D) TOPOLOGY: Linear
```

-continued (iv) ANTI-SENSE: Yes (xi) SEQUENCE DESCRIPTION: SEQ ID NO: 80:

AATGCTTGCT CACACAGGCA TT              22

(2) INFORMATION FOR SEQ ID NO: 81:

(i) SEQUENCE CHARACTERISTICS:
    (A) LENGTH: 18
    (B) TYPE: Nucleic Acid
    (C) STRANDEDNESS: Single
    (D) TOPOLOGY: Linear (iv) ANTI-SENSE: Yes (xi) SEQUENCE DESCRIPTION: SEQ ID NO: 81:

GCCTCGCTAT GGCTCCCA                18

(2) INFORMATION FOR SEQ ID NO: 82:

(i) SEQUENCE CHARACTERISTICS:
    (A) LENGTH: 18
    (B) TYPE: Nucleic Acid
    (C) STRANDEDNESS: Single
    (D) TOPOLOGY: Linear (iv) ANTI-SENSE: Yes (xi) SEQUENCE DESCRIPTION: SEQ ID NO: 82:

CATGGCGCGG GCCGCGGG                18

(2) INFORMATION FOR SEQ ID NO: 83:

(i) SEQUENCE CHARACTERISTICS:
    (A) LENGTH: 20
    (B) TYPE: Nucleic Acid
    (C) STRANDEDNESS: Single
    (D) TOPOLOGY: Linear (iv) ANTI-SENSE: Yes (xi) SEQUENCE DESCRIPTION: SEQ ID NO: 83:

TGCATCCCCC AGGCCACCAT              20

(2) INFORMATION FOR SEQ ID NO: 84:

(i) SEQUENCE CHARACTERISTICS:
    (A) LENGTH: 20
    (B) TYPE: Nucleic Acid
    (C) STRANDEDNESS: Single
    (D) TOPOLOGY: Linear (iv) ANTI-SENSE: Yes (xi) SEQUENCE DESCRIPTION: SEQ ID NO: 84:

TCTGAGTAGC AGAGGAGCTC              20

(2) INFORMATION FOR SEQ ID NO: 85:

(i) SEQUENCE CHARACTERISTICS:
    (A) LENGTH: 20
    (B) TYPE: Nucleic Acid
    (C) STRANDEDNESS: Single
    (D) TOPOLOGY: Linear (iv) ANTI-SENSE: Yes (xi) SEQUENCE DESCRIPTION: SEQ ID NO: 85:

-continued

```
TATGTCTCCC CCACCACTTC                                                  20

(2) INFORMATION FOR SEQ ID NO: 86:

(i) SEQUENCE CHARACTERISTICS:
        (A) LENGTH: 37
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 86:

GCCCCCGACG ACCCTCGGTA TCGCTCCGAC TCCAACG                                37

(2) INFORMATION FOR SEQ ID NO: 87:

(i) SEQUENCE CHARACTERISTICS:
        (A) LENGTH: 8
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 87:

ATAGCGAG                                                                8
```

OLIGONUCLEOTIDE MODULATION OF CELL ADHESION

This application is a continuation of Ser. No: 08/440,740 filed May 12, 1995, now U.S. Pat. No. 5,843,738, which is a is a continuation-in-part of application Ser. No. 08/063,167, filed May 17, 1993, now U.S. Pat. No. 5,514,788, which is a continuation of application Ser. No. 07/969,151, filed Feb. 10, 1993, now abandoned, which is a continuation-in-part of application Ser. No. 08/007,997, filed Jan. 21, 1993, now U.S. Pat. No. 5,591,623, which is a continuation-in-part of application Ser. No. 07/939,855, filed Sep. 2, 1992, now abandoned, which is a continuation-in-part of application Ser. No. 07/567,286 filed Aug. 14, 1990 now abandoned.

FIELD OF THE INVENTION

This invention relates to diagnostics, research reagents and therapies for disease states which respond to modulation of the synthesis or metabolism of cell adhesion molecules. In particular, this invention relates to antisense oligonucleotide interactions with certain messenger ribonucleic acids (mRNAs) or DNAs involved in the synthesis of proteins that regulate adhesion of white blood cells to other white blood cells and to other cell types. Antisense oligonucleotides designed to hybridize to the mRNA encoding intercellular adhesion molecule-1 (ICAM-1), endothelial leukocyte adhesion molecule-1 (ELAM-1, also known as E-selectin), and vascular cell adhesion molecule-1 (VCAM-1) are provided. These oligonucleotides have been found to lead to the modulation of the activity of the RNA or DNA, and thus to the modulation of the synthesis and metabolism of specific cell adhesion molecules. Palliation and therapeutic effect result.

BACKGROUND OF THE INVENTION

Inflammation is a localized protective response elicited by tissues in response to injury, infection, or tissue destruction resulting in the destruction of the infectious or injurious agent and isolation of the injured tissue. A typical inflammatory response proceeds as follows: recognition of an antigen as foreign or recognition of tissue damage, synthesis and release of soluble inflammatory mediators, recruitment of inflammatory cells to the site of infection or tissue damage, destruction and removal of the invading organism or damaged tissue, and deactivation of the system once the invading organism or damage has been resolved. In many human diseases with an inflammatory component, the normal, homeostatic mechanisms which attenuate the inflammatory responses are defective, resulting in damage and destruction of normal tissue.

Cell-cell interactions are involved in the activation of the immune response at each of the stages described above. One of the earliest detectable events in a normal inflammatory response is adhesion of leukocytes to the vascular endothelium, followed by migration of leukocytes out of the vasculature to the site of infection or injury. The adhesion of these leukocytes, or white blood cells, to vascular endothelium is an obligate step in the migration out of the vasculature. Harlan, J. M., *Blood* 1985, 65, 513–525. In general, the first inflammatory cells to appear at the site of inflammation are neutrophils followed by monocytes, and lymphocytes. Cell—cell interactions are also critical for propagation of both B-lymphocytes and T-lymphocytes resulting in enhanced humoral and cellular immune responses, respectively.

The adhesion of white blood cells to vascular endothelium and other cell types is mediated by interactions between specific proteins, termed "adhesion molecules," located on the plasma membrane of both white blood cells and vascular endothelium. The interaction between adhesion molecules is similar to classical receptor ligand interactions with the exception that the ligand is fixed to the surface of a cell instead of being soluble. The identification of patients with a genetic defect in leukocyte adhesion has enabled investigators to identify a family of proteins responsible for adherence of white blood cells. Leukocyte adhesion deficiency (LAD) is a rare autosomal trait characterized by recurrent bacterial infections and impaired pus formation and wound healing. The defect was shown to occur in the common B-subunit of three heterodimeric glycoproteins, Mac-1, LFA-1, and p150,95, normally expressed on the outer cell membrane of white blood cells. Anderson and Springer, *Ann. Rev. Med.* 1987, 38, 175–194. Patients suffering from LAD exhibit a defect in a wide spectrum of adherence-dependent functions of granulocytes, monocytes, and lymphocytes. Three ligands for LFA-1 have been identified, intercellular adhesion molecules 1, 2 and 3 (ICAM-1, ICAM-2 and ICAM-3). Both Mac-1 and p150,95 bind complement fragment C3bi and perhaps other unidentified ligands. Mac-1 also binds ICAM-1.

Other adhesion molecules have been identified which are involved in the adherence of white blood cells to vascular endothelium and subsequent migration out of the vasculature. These include endothelial leukocyte adhesion molecule-1 (ELAM-1), vascular cell adhesion molecule-1 (VCAM-1) and granule membrane protein-140 (GMP-140) and their respective receptors. The adherence of white blood cells to vascular endothelium appears to be mediated in part if not in toto by the five cell adhesion molecules ICAM-1, ICAM-2, ELAM-1, VCAM-1 and GMP-140. Dustin and Springer, *J. Cell Biol.* 1987, 107, 321–331. Expression on the cell surface of ICAM-1, ELAM-1, VCAM-1 and GMP-140 adhesion molecules is induced by inflammatory stimuli. In contrast, expression of ICAM-2 appears to be constitutive and not sensitive to induction by cytokines. In general, GMP-140 is induced by autocoids such as histamine, leukotriene $B_4$, platelet activating factor, and thrombin. Maximal expression on endothelial cells is observed 30 minutes to 1 hour after stimulation, and returns to baseline within 2 to 3 hours. The expression of ELAN-1 and VCAM-1 on endothelial cells is induced by cytokines such as interleukin-1β and tumor necrosis factor, but not gamma-interferon. Maximal expression of ELAM-1 on the surface of endothelial cells occurs 4 to 6 hours after stimulation, and returns to baseline by 16 hours. ELAM-1 expression is dependent on new mRNA and protein synthesis. Elevated VCAM-1 expression is detectable 2 hours following treatment with tumor necrosis factor, is maximal 8 hours following stimulation, and remains elevated for at least 48 hours following stimulation. Rice and Bevilacqua, *Science* 1989, 246, 1303–1306. ICAM-1 expression on endothelial cells is induced by cytokines interleukin-1 tumor necrosis factor and gamma-interferon. Maximal expression of ICAM-1 follows that of ELAM-1 occurring 8 to 10 hours after stimulation and remains elevated for at least 48 hours.

GMP-140 and ELAM-1 are primarily involved in the adhesion of neutrophils to vascular endothelial cells. VCAM-1 primarily binds T and B lymphocytes. In addition, VCAM-1 may play a role in the metastasis of melanoma, and possibly other cancers. ICAM-1 plays a role in adhesion of neutrophils to vascular endothelium, as well as adhesion of monocytes and lymphocytes to vascular endothelium, tissue fibroblasts and epidermal keratinocytes. ICAM-1 also plays a role in T-cell recognition of antigen presenting cell, lysis of target cells by natural killer cells, lymphocyte activation and proliferation, and maturation of T cells in the thymus. In addition, recent data have demonstrated that ICAM-1 is the cellular receptor for the major serotype of rhinovirus, which account for greater than 50% of common colds. Staunton et al., *Cell* 1989, 56, 849–853; Greve et al., *Cell* 1989, 56, 839–847.

Expression of ICAM-1 has been associated with a variety of inflammatory skin disorders such as allergic contact dermatitis, fixed drug eruption, lichen planus, and psoriasis; Ho et al., *J. Am. Acad. Dermatol.* 1990, 22, 64–68; Griffiths and Nickoloff, *Am. J. Pathology* 1989, 135, 1045–1053; Lisby et al., *Br. J. Dermatol.* 1989,120, 479–484; Shiohara et al., *Arch. Dermatol.* 1989, 125, 1371–1376. In addition, ICAM-1 expression has been detected in the synovium of patients with rheumatoid arthritis; Hale et al., *Arth. Rheum.* 1989, 32, 22–30, pancreatic B-cells in diabetes; Campbell et al., *Proc. Natl. Acad. Sci. U.S.A.* 1989, 86, 4282–4286; thyroid follicular cells in patients with Graves' disease; Weetman et al.,*J. Endocrinol.* 1989, 122, 185–191; and with renal and liver allograft rejection; Faull and Russ, *Transplantation* 1989, 48, 226–230; Adams et al., *Lancet* 1989, 1122–1125.

It is has been hoped that inhibitors of ICAM-1, VCAM-1 and ELAN-1 expression would provide a novel therapeutic class of anti-inflammatory agents with activity towards a variety of inflammatory diseases or diseases with an inflammatory component such as asthma, rheumatoid arthritis, allograft rejections, inflammatory bowel disease, various dermatological conditions, and psoriasis. In addition, inhibitors of ICAM-1, VCAM-1, and ELAM-1 may also be effective in the treatment of colds due to rhinovirus infection, AIDS, Kaposi's sarcoma and some cancers and their metastasis. To date, there are no known therapeutic agents which effectively prevent the expression of the cellular adhesion molecules ELAM-1, VCAM-1 and ICAM-1. The use of neutralizing monoclonal antibodies against ICAM-1 in animal models provide evidence that such inhibitors if identified would have therapeutic benefit for asthma; Wegner et al., *Science* 1990, 247, 456–459, renal allografts; Cosimi et al.,*J. Immunol.* 1990, 144, 4604–4612, and cardiac allografts; Isobe et al., *Science* 1992, 255, 1125–1127. The use of a soluble form of ICAM-1 molecule was also effective in preventing rhinovirus infection of cells in culture. Marlin et al., *Nature* 1990, 344, 70–72.

Current agents which affect intercellular adhesion molecules include synthetic peptides, monoclonal antibodies, and soluble forms of the adhesion molecules. To date, synthetic peptides which block the interactions with VCAM-1 or ELAM-1 have not been identified. Monoclonal antibodies may prove to be useful for the treatment of acute inflammatory response due to expression of ICAM-1, VCAM-1 and ELAM-1. However, with chronic treatment, the host animal develops antibodies against the monoclonal antibodies thereby limiting their usefulness. In addition, monoclonal antibodies are large proteins which may have difficulty in gaining access to the inflammatory site. Soluble forms of the cell adhesion molecules suffer from many of the same limitations as monoclonal antibodies in addition to the expense of their production and their low binding affinity. Thus, there is a long felt need for molecules which effectively inhibit intercellular adhesion molecules. Antisense oligonucleotides avoid many of the pitfalls of current agents used to block the effects of ICAM-1, VCAM-1 and ELAM-1.

PCT/US90/02357 (Hession et al.) discloses DNA sequences encoding Endothelial Adhesion Molecules (ELAMs), including ELAM-1 and VCAM-1 and VCAM-1b. A number of uses for these DNA sequences are provided, including (1) production of monoclonal antibody preparations that are reactive for these molecules which may be used as therapeutic agents to inhibit leukocyte binding to endothelial cells; (2) production of ELAM peptides to bind to the ELAM ligand on leukocytes which, in turn, may bind to ELAM on endothelial cells, inhibiting leukocyte binding to endothelial cells; (3) use of molecules binding to ELAMS (such as anti-ELAM antibodies, or markers such as the ligand or fragments of it) to detect inflammation; (4) use of ELAM and ELAM ligand DNA sequences to produce nucleic acid molecules that intervene in ELAM or ELAM ligand expression at the translational level using antisense nucleic acid and ribozymes to block translation of a specific MRNA either by masking MRNA with antisense nucleic acid or cleaving it with a ribozyme. It is disclosed that coding regions are the targets of choice. For VCAM-1, AUG is believed to be most likely; a 15-mer hybridizing to the AUG site is specifically disclosed in Example 17.

OBJECTS OF THE INVENTION

It is a principle object of the invention to provide therapies for diseases with an immunological component, allografts, cancers and metastasis, inflammatory bowel disease, psoriasis and other skin diseases, colds, and AIDS through perturbation in the synthesis and expression of inflammatory cell adhesion molecules.

It is a further object of the invention to provide antisense oligonucleotides which are capable of inhibiting the function of nucleic acids encoding intercellular adhesion proteins.

Yet another object is to provide means for diagnosis of dysfunctions of intercellular adhesion.

These and other objects of this invention will become apparent from a review of the instant specification.

BRIEF DESCRIPTION OF THE DRAWINGS

FIG. 1 is the mRNA sequence of human intercellular adhesion molecule-1 (ICAM-1).

FIG. 2 is the mRNA sequence of human endothelial leukocyte adhesion molecule-1 (ELAM-1).

FIG. 3 is the mRNA sequence of human vascular cell adhesion molecule-1 (VCAM-1).

FIG. 4 is a graphical representation of the induction of ICAM-1 expression on the cell surface of various human cell lines by interleukin-1 and tumor necrosis factor.

SUMMARY OF THE INVENTION

Figure 5:
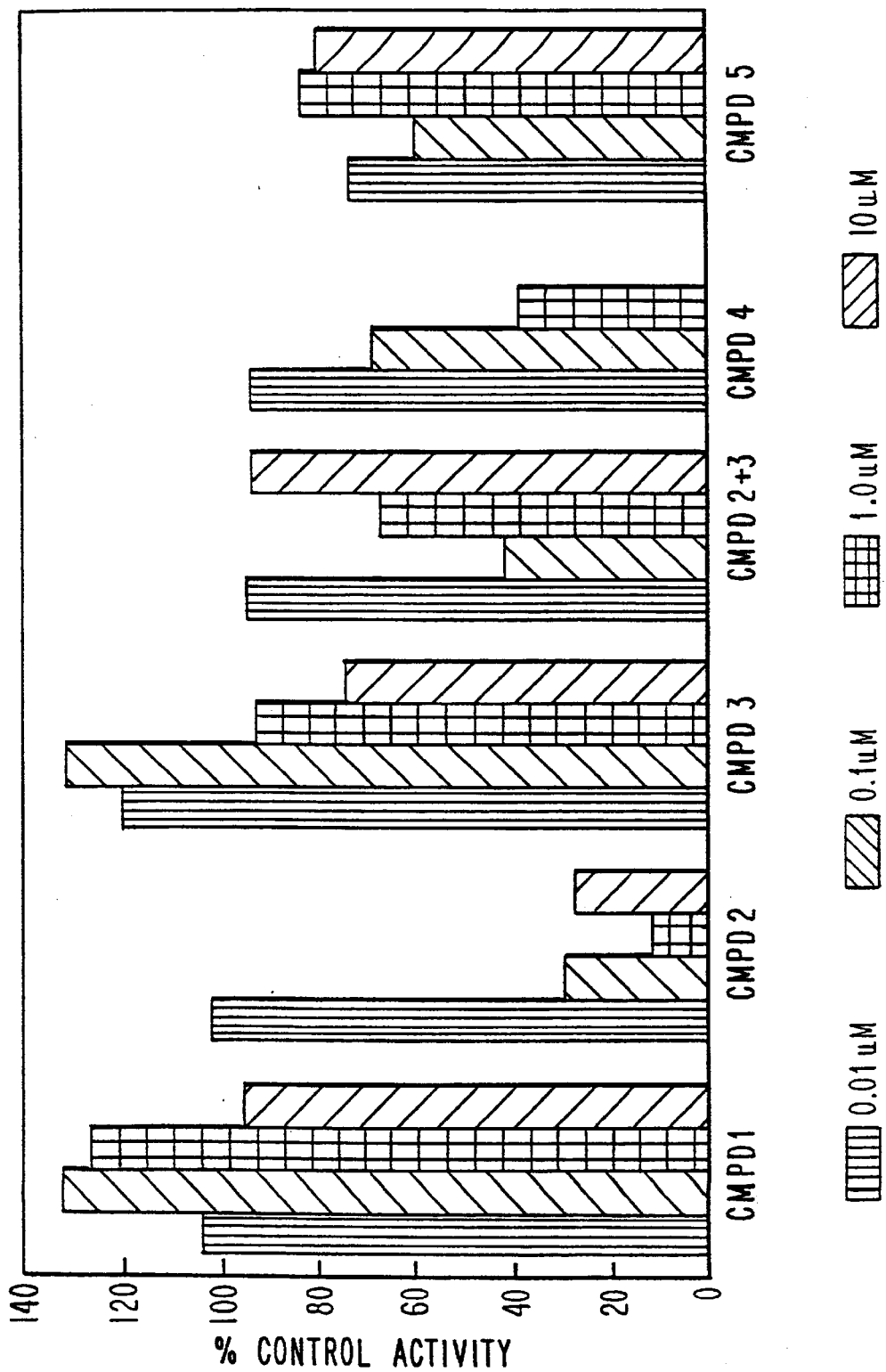
FIG. 5 is a graphical representation of the effects of selected antisense oligonucleotides on ICAM-1 expression on human umbilical vein endothelial cells.

In accordance with the present invention, oligonucleotides are provided which specifically hybridize with nucleic acids encoding intercellular adhesion molecule-1 (ICAM-1), vascular cell adhesion molecule-1 (VCAM-1) and endothelial leukocyte adhesion molecule-1 (ELAM-1). The oligonucleotides are designed to bind either directly to mRNA or to a selected DNA portion forming a triple stranded structure, thereby modulating the amount of mRNA made from the gene. This relationship is commonly denoted as "antisense."

Oligonucleotides are commonly used as research reagents and diagnostics. For example, antisense oligonucleotides, which are able to inhibit gene expression with exquisite specificity, are often used by those of ordinary skill to elucidate the function of particular genes, for example to distinguish between the functions of various members of a biological pathway. This specific inhibitory effect has, therefore, been harnessed for research use. This specificity and sensitivity is also harnessed by those of skill in the art for diagnostic uses.

It is preferred to target specific genes for antisense attack. "Targeting" an oligonucleotide to the associated ribonucleotides, in the context of this invention, is a multi-step process. The process usually begins with identifying a nucleic acid sequence whose function is to be modulated. This may be, as examples, a cellular gene (or mRNA made from the gene) whose expression is associated with a particular disease state, or a foreign nucleic acid from an infectious agent. In the present invention, the target is a cellular gene associated with a particular disease state. The targeting process also includes determination of a site or sites within this region for the oligonucleotide interaction to occur such that the desired effect, either detection of or modulation of expression of the protein, will result. Once the target site or sites have been identified, oligonucleotides are chosen which are sufficiently complementary to the target, i.e., hybridize sufficiently well and with sufficient specificity, to give the desired effect.

It has been discovered that the genes coding for ICAM-1, VCAM-1 and ELAM-1 are particularly useful for this approach. Inhibition of ICAM-1, VCAM-1 and ELAM-1 expression is expected to be useful for the treatment of inflammatory diseases, diseases with an inflammatory component, allograft rejection, psoriasis and other skin diseases, inflammatory bowel disease, cancers and their metastasis, and viral infections.

Methods of modulating cell adhesion comprising contacting the animal with an oligonucleotide hybridizable with nucleic acids encoding a protein capable of modulating cell adhesion are provided. Oligonucleotides hybridizable with an RNA or DNA encoding ICAM-1, VCAM-1 and ELAM-1 are preferred.

The present invention is also useful in diagnostics and in research. Since the oligonucleotides of this invention hybridize to ICAM-1, ELAM-1 or VCAM-1, sandwich and other assays can easily be constructed to exploit this fact. Provision of means for detecting hybridization of an oligonucleotide with one of these intercellular adhesion molecules present in a sample suspected of containing it can routinely be accomplished. Such provision may include enzyme conjugation, radiolabelling or any other suitable detection system. A number of assays may be formulated employing the present invention, which assays will commonly comprise contacting a tissue sample with a detectably labeled oligonucleotide of the present invention under conditions selected to permit hybridization and measuring such hybridization by detection of the label.

For example, radiolabeled oligonucleotides can be prepared by $^{32}P$ labeling at the 5' end with polynucleotide kinase. Sambrook et al., *Molecular Cloning. A Laboratory Manual*, Cold Spring Harbor Laboratory Press, 1989, Volume 2, pg. 10.59. Radiolabeled oligonucleotides are then contacted with tissue or cell samples suspected of containing an intercellular adhesion molecule and the sample is washed to remove unbound oligonucleotide. Radioactivity remaining in the sample indicates bound oligonucleotide (which in turn indicates the presence of an intercellular adhesion molecule) and can be quantitated using a scintillation counter or other routine means. Expression of these proteins can then be detected.

Radiolabeled oligonucleotides of the present invention can also be used to perform autoradiography of tissues to determine the localization, distribution and quantitation of intercellular adhesion molecules for research, diagnostic or therapeutic purposes. In such studies, tissue sections are treated with radiolabeled oligonucleotide and washed as described above, then exposed to photographic emulsion according to routine autoradiography procedures. The emulsion, when developed, yields an image of silver grains over the regions expressing a intercellular adhesion molecule. Quantitation of the silver grains permits expression of these molecules to be detected and permits targeting of oligonucleotides to these areas.

Analogous assays for fluorescent detection of expression of intercellular adhesion molecules can be developed using oligonucleotides of the present invention which are conjugated with fluorescein or other fluorescent tag instead of radiolabeling. Such conjugations are routinely accomplished during solid phase synthesis using fluorescently labeled amidites or CPG (e.g., fluorescein-labeled amidites and CPG available from Glen Research, Sterling Va.).

Each of these assay formats is known in the art. One of skill could easily adapt these known assays for detection of expression of intercellular adhesion molecules in accordance with the teachings of the invention providing a novel and useful means to detect expression of these molecules.

Antisense oligonucleotide inhibition of the expression of intercellular adhesion molecules in vitro is useful as a means to determine a proper course of therapeutic treatment. For example, before a patient is treated with an oligonucleotide composition of the present invention, cells, tissues or a bodily fluid from the patient can be treated with the oligonucleotide and inhibition of expression of intercellular adhesion molecules can be assayed. Effective in vitro inhibition of the expression of molecules in the sample indicates that the expression will also be modulated in vivo by this treatment.

Kits for detecting the presence or absence of intercellular adhesion molecules may also be prepared. Such kits include an oligonucleotide targeted to ICAM-1, ELAM-1 or VCAM-1.

The oligonucleotides of this invention may also be used for research purposes. Thus, the specific hybridization exhibited by the oligonucleotides may be used for assays, purifications, cellular product preparations and in other methodologies which may be appreciated by persons of ordinary skill in the art.

DETAILED DESCRIPTION OF PREFERRED EMBODIMENTS

Antisense oligonucleotides hold great promise as therapeutic agents for the treatment of many human diseases. Oligonucleotides specifically bind to the complementary sequence of either pre-mRNA or mature mRNA, as defined by Watson-Crick base pairing, inhibiting the flow of genetic information from DNA to protein. The properties of antisense oligonucleotides which make them specific for their target sequence also make them extraordinarily versatile. Because antisense oligonucleotides are long chains of four monomeric units they may be readily synthesized for any target RNA sequence. Numerous recent studies have documented the utility of antisense oligonucleotides as biochemical tools for studying target proteins. Rothenberg et al., *J. Natl. Cancer Inst.* 1989, 81, 1539–1544; Zon, G. *Pharmaceutical Res.* 1988, 5, 539–549). Because of recent advances in synthesis of nuclease resistant oligonucleotides, which exhibit enhanced cell uptake, it is now possible to consider the use of antisense oligonucleotides as a novel form of therapeutics.

Antisense oligonucleotides offer an ideal solution to the problems encountered in prior art approaches. They can be designed to selectively inhibit a given isoenzyme, they inhibit the production of the enzyme, and they avoid non-specific mechanisms such as free radical scavenging or binding to multiple receptors. A complete understanding of enzyme mechanisms or receptor-ligand interactions is not needed to design specific inhibitors.

Description of Targets

The acute infiltration of neutrophils into the site of inflammation appears to be due to increased expression of GMP-140, ELAM-1 and ICAM-1 on the surface of endothelial cells. The appearance of lymphocytes and monocytes during the later stages of an inflammatory reaction appear to be mediated by VCAM-1 and ICAM-1. ELAM-1 and GMP-140 are transiently expressed on vascular endothelial cells, while VCAM-1 and ICAM-1 are chronically expressed.

Human ICAM-1 is encoded by a 3.3-kb mRNA resulting in the synthesis of a 55,219 dalton protein (FIG. 1). ICAM-1 is heavily glycosylated through N-linked glycosylation sites. The mature protein has an apparent molecular mass of 90 kDa as determined by SDS-polyacrylamide gel electrophoresis. Staunton et al., *Cell* 1988, 52, 925–933. ICAM-1 is a member of the immunoglobulin supergene family, containing 5 immunoglobulin-like domains at the amino terminus, followed by a transmembrane domain and a cytoplasmic domain. The primary binding site for LFA-1 and rhinovirus are found in the first immunoglobulin-like domain. However, the binding sites appear to be distinct. Staunton et al., *Cell* 1990, 61, 243–354. Recent electron micrographic studies demonstrate that ICAM-1 is a bent rod 18.7 nm in length and 2 to 3 nm in diameter. Staunton et al., *Cell* 1990, 61, 243–254.

ICAM-1 exhibits a broad tissue and cell distribution, and may be found on white blood cells, endothelial cells, fibroblast, keratinocytes and other epithelial cells. The expression of ICAM-1 can be regulated on vascular endothelial cells, fibroblasts, keratinocytes, astrocytes and several cell lines by treatment with bacterial lipopolysaccharide and cytokines such as interleukin-1, tumor necrosis factor, gamma-interferon, and lymphotoxin. See, e.g., Frohman et al., *J. Neuroimmunol.* 1989, 23, 117–124. The molecular mechanism for increased expression of ICAM-1 following cytokine treatment has not been determined.

ELAM-1 is a 115-kDa membrane glycoprotein (FIG. 2) which is a member of the selectin family of membrane glycoproteins. Bevilacqua et al., *Science* 1989, 243, 1160–1165. The amino terminal region of ELAM-1 contains sequences with homologies to members of lectin-like proteins, followed by a domain similar to epidermal growth factor, followed by six tandem 60-amino acid repeats similar to those found in complement receptors 1 and 2. These features are also shared by GMP-140 and MEL-14 antigen, a lymphocyte homing antigen. ELAM-1 is encoded for by a 3.9-kb mRNA. The 3'-untranslated region of ELAM-1 mRNA contains several sequence motifs ATTTA which are responsible for the rapid turnover of cellular mRNA consistent with the transient nature of ELAM-1 expression.

ELAM-1 exhibits a limited cellular distribution in that it has only been identified on vascular endothelial cells. Like ICAM-1, ELAM-1 is inducible by a number of cytokines including tumor necrosis factor, interleukin-1 and lymphotoxin and bacterial lipopolysaccharide. In contrast to ICAM-1, ELAM-1 is not induced by gamma-interferon. Bevilacqua et al., *Proc. Natl. Acad. Sci. USA* 1987, 84, 9238–9242; Wellicome et al., *J. Immunol.* 1990, 144, 2558–2565. The kinetics of ELAM-1 mRNA induction and disappearance in human umbilical vein endothelial cells precedes the appearance and disappearance of ELAM-1 on the cell surface. As with ICAM-1, the molecular mechanism for ELAM-1 induction is not known.

VCAM-1 is a 110-kDa membrane glycoprotein encoded by a 3.2-kb mRNA (FIG. 3). VCAM-1 appears to be encoded by a single-copy gene which can undergo alternative splicing to yield products with either six or seven immunoglobulin domains. Osborn et al., *Cell* 1989, 59, 1203–1211. The receptor for VCAM-1 is proposed to be CD29 (VLA-4) as demonstrated by the ability of monoclonal antibodies to CD29 to block adherence of Ramos cells to VCAM-1. VCAM-1 is expressed primarily on vascular endothelial cells. Like ICAM-1 and ELAM-1, expression of VCAM-1 on vascular endothelium is regulated by treatment with cytokines. Rice and Bevilacqua, *Science* 1989, 246, 1303–1306; Rice et al., *J. Exp. Med.* 1990, 171, 1369–1374. Increased expression appears to be due to induction of the mRNA.

For therapeutics, an animal suspected of having a disease which can be treated by decreasing the expression of ICAM-1, VCAM-1 and ELAM-1 is treated by administering oligonucleotides in accordance with this invention. Oligonucleotides may be formulated in a pharmaceutical composition, which may include carriers, thickeners, diluents, buffers, preservatives, surface active agents, liposomes or lipid formulations and the like, in addition to the oligonucleotide. Pharmaceutical compositions may also include one or more active ingredients such as antimicrobial agents, anti-inflammatory agents, anesthetics, and the like, in addition to oligonucleotide.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable. Coated condoms or gloves may also be useful.

Compositions for oral administration include powders or granules, suspensions or solutions in water or non-aqueous media, capsules, sachets, or tablets. Thickeners, flavorings, diluents, emulsifiers, dispersing aids or binders may be desirable.

Formulations for parenteral administration may include sterile aqueous solutions which may also contain buffers, liposomes, diluents and other suitable additives.

Dosing is dependent on severity and responsiveness of the condition to be treated, but will normally be one or more doses per day, with course of treatment lasting from several days to several months or until a cure is effected or a diminution of disease state is achieved. Persons of ordinary skill can easily determine optimum dosages, dosing methodologies and repetition rates.

The present invention employs oligonucleotides for use in antisense inhibition of the function of RNA and DNA corresponding to proteins capable of modulating inflammatory cell adhesion. In the context of this invention, the term "oligonucleotide" refers to an oligomer or polymer of ribonucleic acid or deoxyribonucleic acid. This term includes oligomers consisting of naturally occurring bases, sugars and intersugar (backbone) linkages as well as oligomers having non-naturally occurring portions which function similarly. Such modified or substituted oligonucleotides are often preferred over native forms because of properties such as, for example, enhanced cellular uptake and increased stability in the presence of nucleases.

Specific examples of some preferred oligonucleotides envisioned for this invention may contain phosphorothioates, phosphotriesters, methyl phosphonates, short chain alkyl or cycloalkyl intersugar linkages or short chain heteroatomic or heterocyclic intersugar linkages. Most preferred are those with $CH_2$—NH—O—$CH_2$, $CH_2$—N($CH_3$)—O—$CH_2$, $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—P—O—$CH_2$). Also preferred are oligonucleotides having morpholino backbone structures. Summerton, J. E. and Weller, D. D., U.S. Pat. No. 5,034,506. In other preferred embodiments, such as the protein-nucleic acid (PNA) backbone, the phosphodiester backbone of the oligonucleotide may be replaced with a polyamide backbone, the bases being bound directly or indirectly to the aza nitrogen atoms of the polyamide backbone. P. E. Nielsen, M. Egholm, R. H. Berg, O. Buchardt, *Science* 1991, 254, 1497. Other preferred oligonucleotides may contain alkyl and halogen-substituted sugar moieties comprising one of the following at the 2' position: OH, SH, $SCH_3$, F, OCN, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O—, S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a conjugate; a reporter group; an intercalator; a group for improving the pharmacokinetic properties of an oligonucleotide; or a group for improving the pharmacodynamic properties of an oligonucleotide and other substituents having similar properties. Oligonucleotides may also have sugar mimetics such as cyclobutyls in place of the pencofuranosyl group.

The oligonucleotides in accordance with this invention preferably comprise from about 3 to about 50 nucleic acid base units. It is more preferred that such oligonucleotides comprise from about 8 to 25 nucleic acid base units, and still more preferred to have from about 12 to 22 nucleic acid base units. As will be appreciated, a nucleic acid base unit is a base-sugar combination suitably bound to an adjacent nucleic acid base unit through phosphodiester or other bonds.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; however, the actual synthesis of the oligonucleotides are well within the talents of the routineer. It is also well known to use similar techniques to prepare other oligonucleotides such as the phosphorothioates and alkylated derivatives.

In accordance with this invention, persons of ordinary skill in the art will understand that messenger RNA identified by the open reading frames (ORFs) of the DNA from which they are transcribed includes not only the information from the ORFs of the DNA, but also associated ribonucleotides which form regions known to such persons as the 5'-untranslated region, the 3'- untranslated region, and intervening sequence ribonucleotides. Thus, oligonucleotides may be formulated in accordance with this invention which are targeted wholly or in part to these associated ribonucleotides as well as to the informational ribonucleotides. In preferred embodiments, the oligonucleotide is specifically hybridizable with a transcription initiation site, a translation initiation site, an intervening sequence and sequences in the 3'-untranslated region.

In accordance with this invention, the oligonucleotide is specifically hybridizable with portions of nucleic acids encoding a protein involved in the adhesion of white blood cells either to other white blood cells or other cell types. In preferred embodiments, said proteins are intercellular adhesion molecule-1, vascular cell adhesion molecule-1 and endothelial leukocyte adhesion molecule-1. Oligonucleotides comprising the corresponding sequence, or part thereof, are useful in the invention. For example, FIG. 1 is a human intercellular adhesion molecule-1 mRNA sequence. A preferred sequence segment which may be useful in whole or in part is:

| 5' | 3' | SEQ ID NO: |
|---|---|---|
| TGGGAGCCATAGCGAGGC | | 1 |
| GAGGAGCTCAGCGTCGACTG | | 2 |
| GACACTCAATAAATAGCTGGT | | 3 |
| GAGGCTGAGGTGGGAGGA | | 4 |
| CGATGGGCAGTGGGAAAG | | 5 |
| GGGCGCGTGATCCTTATAGC | | 6 |
| CATAGCGAGGCTGAGGTTGC | | 7 |
| CGGGGGCTGCTGGGAGCCAT | | 8 |
| TCAGGGAGGCGTGGCTTGTG | | 13 |
| CCTGTCCCGGGATAGGTTCA | | 14 |
| TTGAGAAAGCTTTATTAACT | | 16 |
| CCCCCACCACTTCCCCTCTC. | | 15 |

FIG. 2 is a human endothelial leukocyte adhesion molecule-1 mRNA sequence. A preferred sequence segment which may be useful in whole or in part is:

| 5' | 3' | SEQ ID NO: |
|---|---|---|
| CAATCATGACTTCAAGAGTTCT | | 28 |
| TCACTGCTGCCTCTGTCTCAGG | | 73 |
| TGATTCTTTTGAACTTAAAAGGA | | 74 |
| TTAAAGGATGTAAGAAGGCT | | 75 |
| CATAAGCACATTTATTGTC | | 76 |
| TTTTGGGAAGCAGTTGTTCA | | 77 |
| AACTGTGAAGCAATCATGACT | | 78 |
| CCTTGAGTGGTGCATTCAACCT | | 79 |
| AATGCTTGCTCACACAGGCATT. | | 80 |

FIG. 3 is a human vascular cell adhesion molecule-1 mRNA sequence. A preferred sequence segment which may be useful in whole or in part is:

| 5' | 3' | SEQ ID NO: |
|---|---|---|
| CCAGGCATTTTAAGTTGCTGT | | 40 |
| CCTGAAGCCAGTGAGGCCCG | | 41 |
| GATGAGAAAATAGTGGAACCA | | 42 |
| CTGAGCAAGATATCTAGAT | | 43 |
| CTACACTTTTGATTTCTGT | | 44 |
| TTGAACATATCAAGCATTAGCT | | 45 |
| TTTACATATGTACAAATTATGT | | 46 |
| AATTATCACTTTACTATACAAA | | 47 |
| AGGGCTGACCAAGACGGTTGT. | | 48 |

While the illustrated sequences are believed to be accurate, the present invention is directed to the correct sequences, should errors be found. Oligonucleotides useful in the invention comprise one of these sequences, or part thereof. Thus, it is preferred to employ any of these oligonucleotides as set forth above or any of the similar oligonucleotides which persons of ordinary skill in the art can prepare from knowledge of the preferred antisense targets for the modulation of the synthesis of inflammatory cell adhesion molecules.

Several preferred embodiments of this invention are exemplified in accordance with the following nonlimiting examples. The target mRNA species for modulation relates to intercellular adhesion molecule-1, endothelial leukocyte adhesion molecule-1, and vascular cell adhesion molecule-1. Persons of ordinary skill in the art will appreciate that the present invention is not so limited, however, and that it is generally applicable. The inhibition or modulation of production of the ICAM-1 and/or ELAM-1 and/or VCAM-1 are expected to have significant therapeutic benefits in the treatment of disease. In order to assess the effectiveness of the compositions, an assay or series of assays is required.

The following examples are provided for illustrative purposes only and are not intended to limit the invention.

EXAMPLES

Example 1

Expression of ICAM-1, VCAM-1 and ELAM-1 on the surface of cells can be quantitated using specific monoclonal antibodies in an ELISA. Cells are grown to confluence in 96 well microliter plates. The cells are stimulated with either interleukin-1 or tumor necrosis factor for 4 to 8 hours to quantitate ELAM-1 and 8 to 24 hours to quantitate ICAM-1 and VCAM-1. Following the appropriate incubation time with the cytokine, the cells are gently washed three times with a buffered isotonic solution containing calcium and magnesium such as Dulbecco's phosphate buffered saline (D-PBS). The cells are then directly fixed on the microtiter plate with 1 to 2% paraformaldehyde diluted in D-PBS for 20 minutes at 25° C. The cells are washed again with D-PBS three times. Nonspecific binding sites on the microtiter plate are blocked with 2% bovine serum albumin in D-PBS for 1 hour at 37° C. Cells are incubated with the appropriate monoclonal antibody diluted in blocking solution for 1 hour at 37° C. Unbound antibody is removed by washing the cells three times with D-PBS. Antibody bound to the cells is detected by incubation with a 1:1000 dilution of biotinylated goat anti-mouse IgG (Bethesda Research Laboratories, Gaithersberg, Md.) in blocking solution for 1 hour at 37° C. Cells are washed three times with D-PBS and then incubated with a 1:1000 dilution of streptavidin conjugated to β-galactosidase (Bethesda Research Laboratories) for 1 hour at 37° C. The cells are washed three times with D-PBS for 5 minutes each. The amount of β-galactosidase bound to the specific monoclonal antibody is determined by developing the plate in a solution of 3.3 mM chlorophenolred-β-D-galactopyranoside, 50 mM sodium phosphate, 1.5 mM $MgCl_2$; pH=7.2 for 2 to 15 minutes at 37° C. The concentration of the product is determined by measuring the absorbance at 575 nm in an ELISA microtiter plate reader.

An example of the induction of ICAM-1 observed following stimulation with either interleukin-1β or tumor necrosis factor α in several human cell lines is shown in FIG. 4. Cells were stimulated with increasing concentrations of interleukin-1 or tumor necrosis factor for 15 hours and processed as described above. ICAM-1 expression was determined by incubation with a 1:1000 dilution of the monoclonal antibody 84H10 (Amac Inc., Westbrook, Me.). The cell lines used were passage 4 human umbilical vein endothelial cells (HUVEC), a human epidermal carcinoma cell line (A431), a human melanoma cell line (SK-MEL-2) and a human lung carcinoma cell line (A549). ICAM-1 was induced on all the cell lines, however, tumor necrosis factor was more effective than interleukin-1 in induction of ICAM-1 expression on the cell surface (FIG. 4).

Screening antisense oligonucleotides for inhibition of ICAM-1, VCAM-1 or ELAM-1 expression is performed as described above with the exception of pretreatment of cells with the oligonucleotides prior to challenge with the cytokines. An example of antisense oligonucleotide inhibition of ICAM-1 expression is shown in FIG. 5. Human umbilical vein endothelial cells (HUVEC) were treated with increasing concentration of oligonucleotide diluted in Opti MEM (GIBCO, Grand Island, N.Y.) containing 8 μM N-[1-(2,3-dioleyloxy) propyl]-N,N,N-trimethylammonium chloride (DOTMA) for 4 hours at 37° C. to enhance uptake of the oligonucleotides. The medium was removed and replaced with endothelial growth medium (EGM-UV; Clonetics, San Diego, Calif.) containing the indicated concentration of oligonucleotide for an additional 4 hours. Interleukin-1β was added to the cells at a concentration of 5 units/ml and incubated for 14 hours at 37° C. The cells were quantitated for ICAM-1 expression using a 1:1000 dilution of the monoclonal antibody 84H10 as described above. The oligonucleotides used were:

COMPOUND 1—(ISIS 1558) a phosphodiester oligonucleotide designed to hybridize with position 64–80 of the mRNA covering the AUG initiation of translation codon having the sequence

| 5'-TGGGAGCCATAGCGAGGC-3' | (SEQ ID NO: 1). |
|---|---|

COMPOUND 2—(ISIS 1570) a phosphorothioate containing oligonucleoeide corresponding to the same sequence as COMPOUND COMPOUND 3—a phosphorothioate oligonucleotide complementary to COMPOUND 1 and COMPOUND 2 exhibiting the sequence

5'-GCCTCGCTATGGCTCCCA-3' (SEQ ID NO: 81).

COMPOUND 4—(ISIS 1572) a phosphorothioate containing oligonucleotide designed to hybridize to positions 2190–2210 of the mRNA in the 3' untranslated region containing the sequence

5'-GACACTCAATAAATAGCTGGT-3' (SEQ ID NO: 3).

COMPOUND 5—(ISIS 1821) a phosphorothioate containing oligonucleotide designed to hybridize to human 5-lipoxygenase mRNA used as a control containing the sequence

5'-CATGGCGCGGGCCGCGGG-3' (SEQ ID NO: 82).

The phosphodiester oligonucleotide targeting the AUG initiation of translation region of the human ICAM-1 mRNA (COMPOUND 1) did not inhibit expression of ICAM-1; however, the corresponding phosphorothioate containing oligonucleotide (COMPOUND 2) inhibited ICAM-1 expression by 70% at a concentration of 0.1 μM and 90% at 1 μM concentration (FIG. 4). The increased potency of the phosphorothioate oligonucleotide over the phosphodiester is probably due to increased stability. The sense strand to COMPOUND 2, COMPOUND 3, modestly inhibited ICAM-1 expression at 10 μM. If COMPOUND 2 was prehybridized to COMPOUND 3 prior to addition to the cells, the effects of COMPOUND 2 on ICAM-1 expression were attenuated suggesting that the activity of COMPOUND 2 was due to antisense oligonucleotide effect, requiring hybridization to the mRNA. The antisense oligonucleotide directed against 3' untranslated sequences (COMPOUND 4) inhibited ICAM-1 expression 62% at a concentration of 1 μM (FIG. 5). The control oligonucleotide, targeting human 5-lipoxygenase (COMPOUND 5) reduced ICAM-1 expression by 20%. These data demonstrate that oligonucleotides are capable of inhibiting ICAM-1 expression on human umbilical vein endothelial cells and suggest that the inhibition of ICAM-1 expression is due to an antisense activity.

Figure 6A:
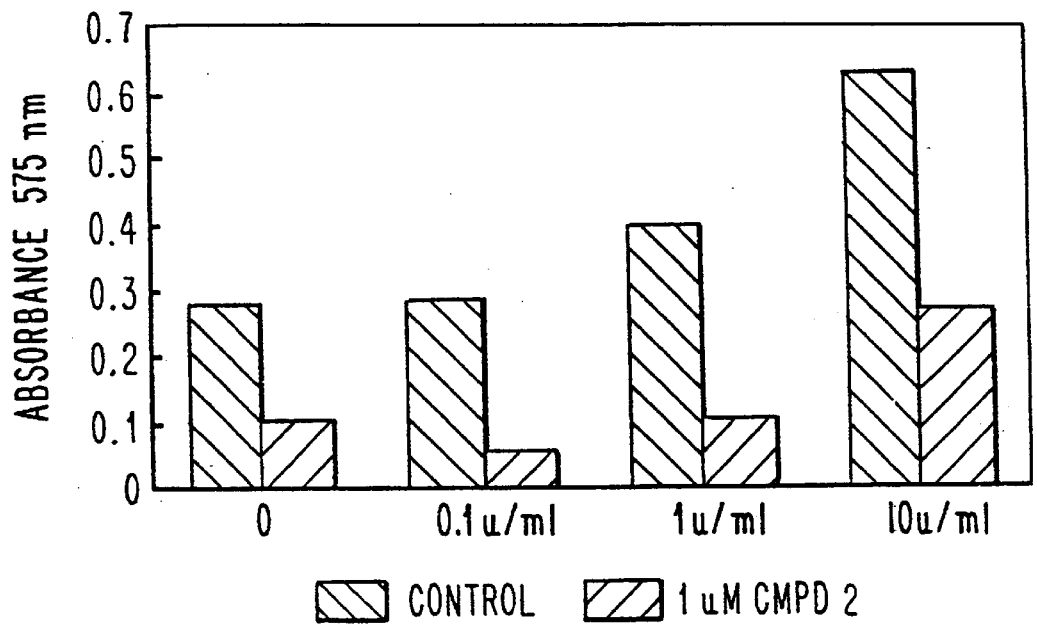
FIGS. 6A and 6B are a graphical representation of the effects of an antisense oligonucleotide on the expression of ICAM-1 in human umbilical vein endothelial cells stimulated with tumor necrosis factor and interleukin-1.
Figure 6B:
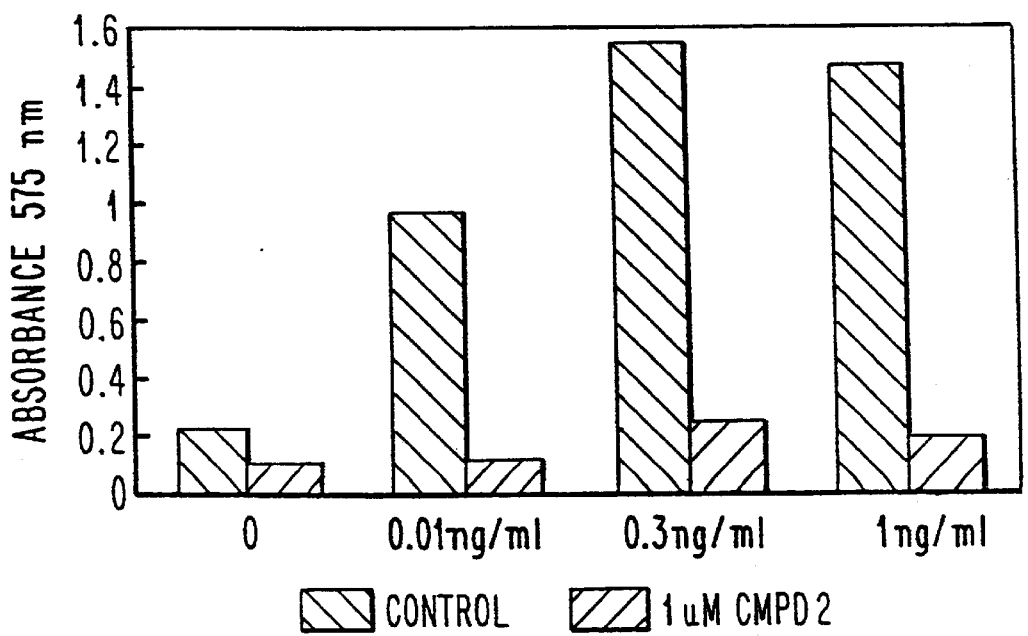

The antisense oligonucleotide COMPOUND 2 at a concentration of 1 μM inhibits expression of ICAM-1 on human umbilical vein endothelial cells stimulated with increasing concentrations of tumor necrosis factor and interleukin-1 (FIG. 6). These data demonstrate that the effects of COMPOUND 2 are not specific for interleukin-1 stimulation of cells.

Analogous assays can also be used to demonstrate inhibition of ELAM-1 and VCAM-1 expression by antisense oligonucleotides.

Example 2

A second cellular assay which can be used to demonstrate the effects of antisense oligonucleotides on ICAM-1, VCAM-1 or ELAM-1 expression is a cell adherence assay. Target cells are grown as a monolayer in a multiwell plate, treated with oligonucleotide followed by cytokine. The adhering cells are then added to the monolayer cells and incubated for 30 to 60 minutes at 37° C. and washed to remove nonadhering cells. Cells adhering to the monolayer may be determined either by directly counting the adhering cells or prelabeling the cells with a radioisotope such as $^{51}Cr$ and quantitating the radioactivity associated with the monolayer as described. Dustin and Springer, *J. Cell Biol.* 1988, 107, 321–331. Antisense oligonucleotides may target either ICAM-1, VCAM-1 or ELAM-1 in the assay.

Figure 7:
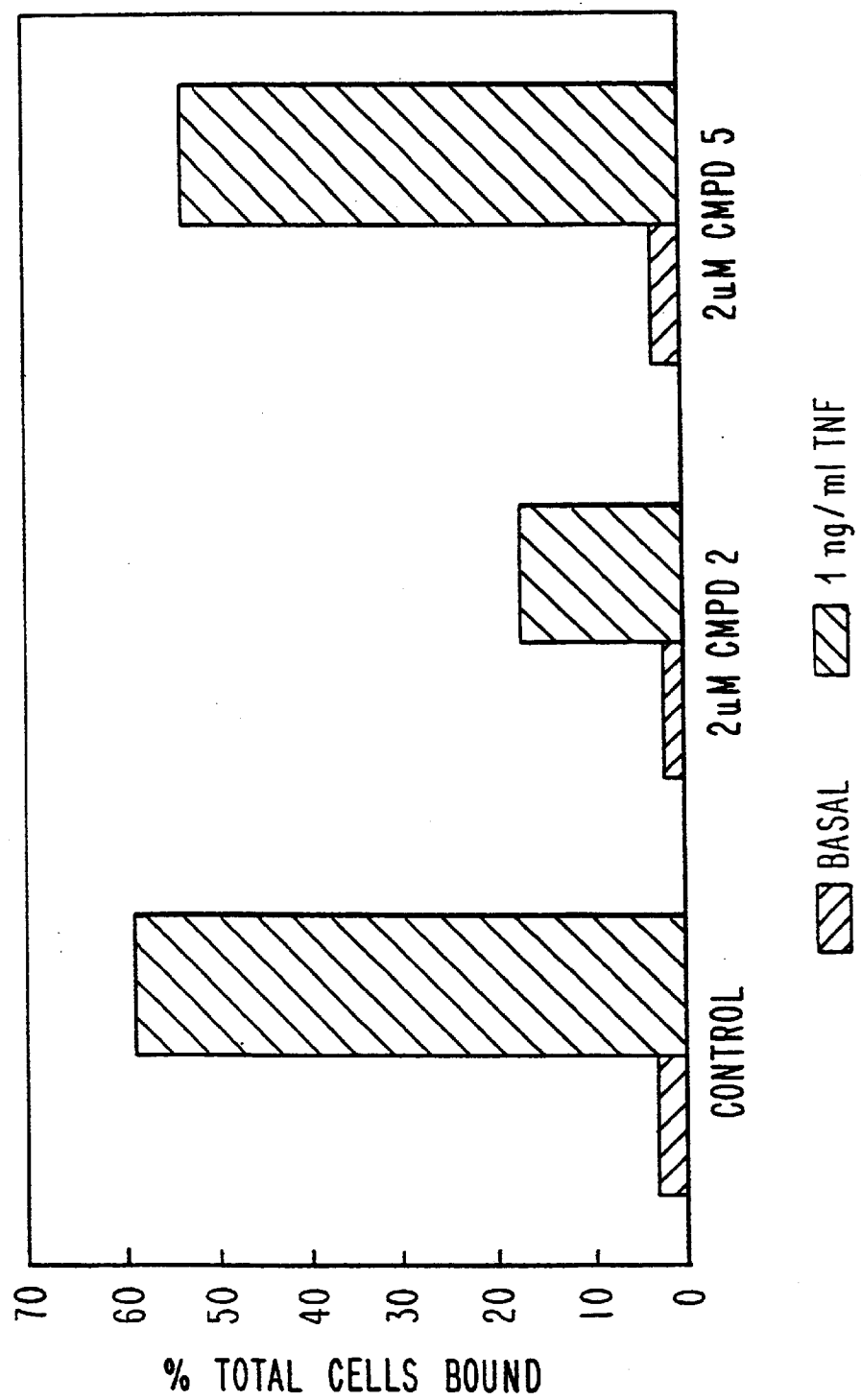
FIG. 7 is a graphical representation of the effect of antisense oligonucleotides on ICAM-1 mediated adhesion of DMSO differentiated HL-60 cells to control and tumor necrosis factor treated human umbilical vein endothelial cells.

An example of the effects of antisense oligonucleotides targeting ICAM-1 mRNA on the adherence of DMSO differentiated HL-60 cells to tumor necrosis factor treated human umbilical vein endothelial cells is shown in FIG. 7. Human umbilical vein endothelial cells were grown to 80% confluence in 12 well plates. The cells were treated with 2 μM oligonucleotide diluted in Opti-MEM containing 8 μM DOTMA for 4 hours at 37° C. The medium was removed and replaced with fresh endothelial cell growth medium (EGM-UV) containing 2 μM of the indicated oligonucleotide and incubated 4 hours at 37° C. Tumor necrosis factor, 1 ng/ml, was added to cells as indicated and cells incubated for an additional 19 hours. The cells were washed once with EGM-UV and $1.6 \times 10^5$ HL-60 cells differentiated for 4 days with 1.3% DMSO added. The cells were allowed to attach for 1 hour at 37° C. and gently washed 4 times with Dulbecco's phosphate-buffered saline (D-PBS) warmed to 37° C. Adherent cells were detached from the monolayer by addition of 0.25 ml of cold (40° C.) phosphate-buffered saline containing 5 mM EDTA and incubated on ice for 5 minutes. The number of cells removed by treatment with EDTA was determined by counting with a hemocytometer. Endothelial cells detached from the monolayer by EDTA treatment could easily be distinguished from HL-60 cells by morphological differences.

In the absence of tumor necrosis factor, 3% of the HL-60 cells bound to the endothelial cells. Treatment of the endothelial cell monolayer with 1 ng/ml tumor necrosis factor increased the number of adhering cells to 59% of total cells added (FIG. 7). Treatment with the antisense oligonucleotide COMPOUND 2 or the control oligonucleotide COMPOUND 5 did not change the number of cells adhering to the monolayer in the absence of tumor necrosis factor treatment (FIG. 7). The antisense oligonucleotide, COMPOUND 2 reduced the number of adhering cells from 59% of total cells added to 17% of the total cells added (FIG. 7). In contrast, the control oligonucleotide COMPOUND 5 did not significantly reduce the number of cells adhering to the tumor necrosis factor treated endothelial monolayer, i.e., 53% of total cells added for COMPOUND 5 treated cells versus 59% for control cells.

These data indicate that antisense oligonucleotides are capable of inhibiting ICAM-1 expression on endothelial cells and that inhibition of ICAM-1 expression correlates with a decrease in the adherence of a neutrophil-like cell to the endothelial monolayer in a sequence specific fashion. Because other molecules also mediate adherence of white blood cells to endothelial cells, such as ELAM-1, and V(CAM-1 it is not expected that adherence would be completely blocked.

Example 3

Synthesis and Characterization of Oligonucleotides

Unmodified DNA oligonucleotides were synthesized on an automated DNA synthesizer (Applied Biosystems model 380B) using standard phosphoramidite chemistry with oxidation by iodine. β-cyanoethyldiisopropyl-phosphoramidites were purchased from Applied Biosystems (Foster City, Calif.). For phosphorothioate oligonucleotides, the standard oxidation bottle was replaced by a 0.2 M solution of 3H-1,2-benzodithiole-3-one 1,1-dioxide in acetonitrile for the stepwise thiation of the phosphite linkages. The thiation cycle wait step was increased to 68 seconds and was followed by the capping step.

2'-O-methyl phosphorothioate oligonucleotides were synthesized using 2'-O-methyl β-cyanoethyldiisopropyl-phosphoramidites (Chemgenes, Needham Mass.) and the standard cycle for unmodified oligonucleotides, except the wait step after pulse delivery of tetrazole and base was increased to 360 seconds. The 3'-base used to start the synthesis was a 2'-deoxyribonucleotide.

2'-fluoro phosphorothioate oligonucleotides were synthesized using 5'-dimethoxytrityl-3'-phosphoramidites and prepared as disclosed in U.S. patent application Ser. Nos. 463,358, filed Jan. 11, 1990, and 566,977, filed Aug. 13, 1990, which are assigned to the same assignee as the instant application and which are incorporated by reference herein. The 2'-fluoro oligonucleotides were prepared using phosphoramidite chemistry and a slight modification of the standard DNA synthesis protocol: deprotection was effected using methanolic ammonia at room temperature.

After cleavage from the controlled pore glass column (Applied Biosystems) and deblocking in concentrated ammonium hydroxide at 55° C. for 18 hours, the oligonucleotides were purified by precipitation twice out of 0.5 M NaCl with 2.5 volumes ethanol. Analytical gel electrophoresis was accomplished in 20%. acrylamide, 8 M urea, 45 mM Tris-borate buffer, pH 7.0. Oligodeoxynucleotides and phosphorothioate oligonucleotides were judged from electrophoresis to be greater than 80% full length material.

RNA oligonucleotide synthesis was performed on an ABI model 380B DNA synthesizer. The standard synthesis cycle was modified by increasing the wait step after the pulse delivery of tetrazole to 900 seconds. The bases were deprotected by incubation in methanolic ammonia overnight. Following base deprotections the oligonucleotides were dried in vacuo. The t-butyldimethylsilyl protecting the 2' hydroxyl was removed by incubating the oligonucleotide in 1 M tetrabutylammonium-fluoride in tetrahydrofuran overnight. The RNA oligonucleotides were further purified on $C_{18}$ Sep-Pak cartridges (Waters, Division of Millipore Corp., Milford Mass.) and ethanol precipitated.

The relative amounts of phosphorothioate and phosphodiester linkages obtained by this synthesis were periodically checked by $^{31}P$ NMR spectroscopy. The spectra were obtained at ambient temperature using deuterium oxide or dimethyl sulfoxide-$d_6$ as solvent. Phosphorothioate samples typically contained less than one percent of phosphodiester linkages.

Secondary evaluation was performed with oligonucleotides purified by trityl-on HPLC on a PRP-1 column (Hamilton Co., Reno, Nev.) using a gradient of acetonitrile in 50 mM triethylammonium acetate, pH 7.0 (4% to 32% in 30 minutes, flow rate=1.5 ml/min). Appropriate fractions were pooled, evaporated and treated with 5% acetic acid at ambient temperature for 15 minutes. The solution was extracted with an equal volume of ethyl acetate, neutralized with ammonium hydroxide, frozen and lyophilized. HPLC-purified oligonucleotides were not significantly different in potency from precipitated oligonucleotides, as judged by the ELISA assay for ICAM-1 expression.

Example 4

Cell Culture and Treatment with Oligonucleotides

The human lung carcinoma cell line A549 was obtained from the American Type Culture Collection (Bethesda Md.). Cells were grown in Dulbecco's Modified Eagle's Medium (Irvine Scientific, Irvine Calif.) containing 1 gm glucose/liter and 10% fetal calf serum (Irvine Scientific). Human umbilical vein endothelial cells (HUVEC) (Clonetics, San Diego Calif.) were cultured in EGM-UV medium (Clonetics). HUVEC were used between the second and sixth passages. Human epidermal carcinoma A431 cells were obtained from the American Type Culture Collection and cultured in DMEM with 4.5 g/l glucose. Primary human keratinocytes were obtained from Clonetics and grown in KGM (Keratinocyte growth medium, Clonetics).

Cells grown in 96-well plates were washed three times with Opti-MEM (GIBCO, Grand Island, N.Y.) prewarmed to 37° C. 100 μl of Opti-MEM containing either 10 μg/ml N-[1-(2,3-dioleyloxy)propyl]-N,N,N-trimethylammonium chloride (DOTMA, Bethesda Research Labs, Bethesda, Md.) in the case of HUVEC cells or 20 μg/ml DOTMA in the case of A549 cells was added to each well. Oligonucleotides were sterilized by centrifugation through 0.2 μm Centrex cellulose acetate filters (Schleicher and Schuell, Keene, N.H.). Oligonucleotides were added as 20×stock solution to the wells and incubated for 4 hours at 37° C. Medium was removed and replaced with 150 μl of the appropriate growth medium containing the indicated concentration of oligonucleotide. Cells were incubated for an additional 3 to 4 hours at 37° C. then stimulated with the appropriate cytokine for 14 to 16 hours, as indicated. ICAM-1 expression was determined as described in Example 1. The presence of DOTMA during the first 4 hours incubation with oligonucleotide increased the potency of the oligonucleotides at least 100-fold. This increase in potency correlated with an increase in cell uptake of the oligonucleotide.

Example 5

ELISA Screening of Additional Antisense Oligonucleotides for Activity against ICAM-1 Gene Expression in Interleukin-1β-Stimulated Cells Antisense oligonucleotides were originally designed that would hybridize to five target sites on the human ICAM-1 mRNA. Oligonucleotides were synthesized in both phosphodiester (P=O; ISIS 1558, 1559, 1563, 1564 and 1565) and phosphorothioate (P=S; ISIS 1570, 1571, 1572, 1573, and 1574) forms. The oligonucleotides are shown in Table 1.

TABLE 1

ANTISENSE OLIGONUCLEOTIDES
WHICH TARGET HUMAN ICAM-1

| ISIS NO. | SEQ ID NO. | TARGET REGION | MODIFICATION |
|---|---|---|---|
| 1558 | 1 | AUG Codon (64–81) | P = O |
| 1559 | 2 | 5'-Untranslated (32–49) | P = O |
| 1563 | 3 | 3'-Untranslated (2190–3010) | P = O |
| 1564 | 4 | 3'-Untranslated (2849–2866) | P = O |
| 1565 | 5 | Coding Region (1378–1395) | P = O |
| 1570 | 1 | AUG Codon (64–81) | P = S |
| 1571 | 2 | 5'-Untranslated (32–49) | P = S |
| 1572 | 3 | 3'-Untranslated (2190–3010) | P = S |
| 1573 | 4 | 3'-Untranslated (2849–2866) | P = S |

TABLE 1-continued

ANTISENSE OLIGONUCLEOTIDES
WHICH TARGET HUMAN ICAM-1

| ISIS NO. | SEQ ID NO. | TARGET REGION | MODIFICATION |
|---|---|---|---|
| 1574 | 5 | Coding Region (1378–1395) | P = S |
| 1930 | 6 | 5'-Untranslated (1–20) | P = S |
| 1931 | 7 | AUG Codon (55–74) | P = S |
| 1932 | 8 | AUG Codon (72–91) | P = S |
| 1933 | 9 | Coding Region (111–130) | P = S |
| 1934 | 10 | Coding Region (351–370) | P = S |
| 1935 | 11 | Coding Region (889–908) | P = S |
| 1936 | 12 | Coding Region (1459–1468) | P = S |
| 1937 | 13 | Termination Codon (1651–1687) | P = S |
| 1938 | 14 | Termination Codon (1668–1687) | P = S |
| 1939 | 15 | 3'-Untranslated (1952–1971) | P = S |
| 1940 | 16 | 3'-Untranslated (2975–2994) | P = S |
| 2149 | 17 | AUG Codon (64–77) | P = S |
| 2163 | 18 | AUG Codon (64–75) | P = S |
| 2164 | 19 | AUG Codon (64–73) | P = S |
| 2165 | 20 | AUG Codon (66–80) | P = S |
| 2173 | 21 | AUG Codon (64–79) | P = S |
| 2302 | 22 | 3'-Untranslated (2114–2133) | P = S |
| 2303 | 23 | 3'-Untranslated (2039–2058) | P = S |
| 2304 | 24 | 3'-Untranslated (1895–1914) | P = S |
| 2305 | 25 | 3'-Untranslated (1935–1954) | P = S |
| 2307 | 26 | 3'-Untranslated (1976–1995) | P = S |
| 2634 | 1 | AUG-Codon (64–81) | 2'-fluoro A, C & U; P = S |
| 2637 | 15 | 3'-Untranslated (1952–1971) | 2'-fluoro A, C & U; |
| 2691 | 1 | AUG Codon (64–81) | P = O, except last 3 bases, P = S |
| 2710 | 15 | 3'-Untranslated (1952–1971) | 2'-O-methyl; P = O |
| 2711 | 1 | AUG Codon (64–81) | 2'-O-methyl; P = O |
| 2973 | 15 | 3'-Untranslated (1952–1971) | 2'-O-methyl; P = S |
| 2974 | 1 | AUG Codon (64–81) | 2'-O-methyl; P = S |
| 3064 | 27 | 5'-CAP (32–51) | P = S; G & C added as spacer to 3' |
| 3067 | 84 | 5'-CAP (32–51) | P = S |
| 3222 | 84 | 5'-CAP (32–51) | 2'-O-methyl; P = O |
| 3224 | 84 | 5'-CAP (32–51) | 2'-O-methyl; P = S |
| 3581 | 85 | 3'-Untranslated (1959–1978) | P = S |

Inhibition of ICAM-1 expression on the surface of interleukin-1β-stimulated cells by the oligonucleotides was determined by ELISA assay as described in Example 1. The oligonucleotides were tested in two different cell lines. None of the phosphodiester oligonucleotides inhibited ICAM-1 expression. This is probably due to the rapid degradation of phosphodiester oligonucleotides in cells. Of the five phosphorothioate oligonucleotides, the most active was ISIS 1570, which hybridizes to the AUG translation initiation codon. A 2'-o-methyl phosphorothioate oligonucleotide, ISIS 2974, was approximately threefold less effective than ISIS 1570 in inhibiting ICAM-1 expression in HUVEC and A549 cells. A 2'-fluoro oligonucleotide, ISIS 2634, was also less effective.

Figure 8:
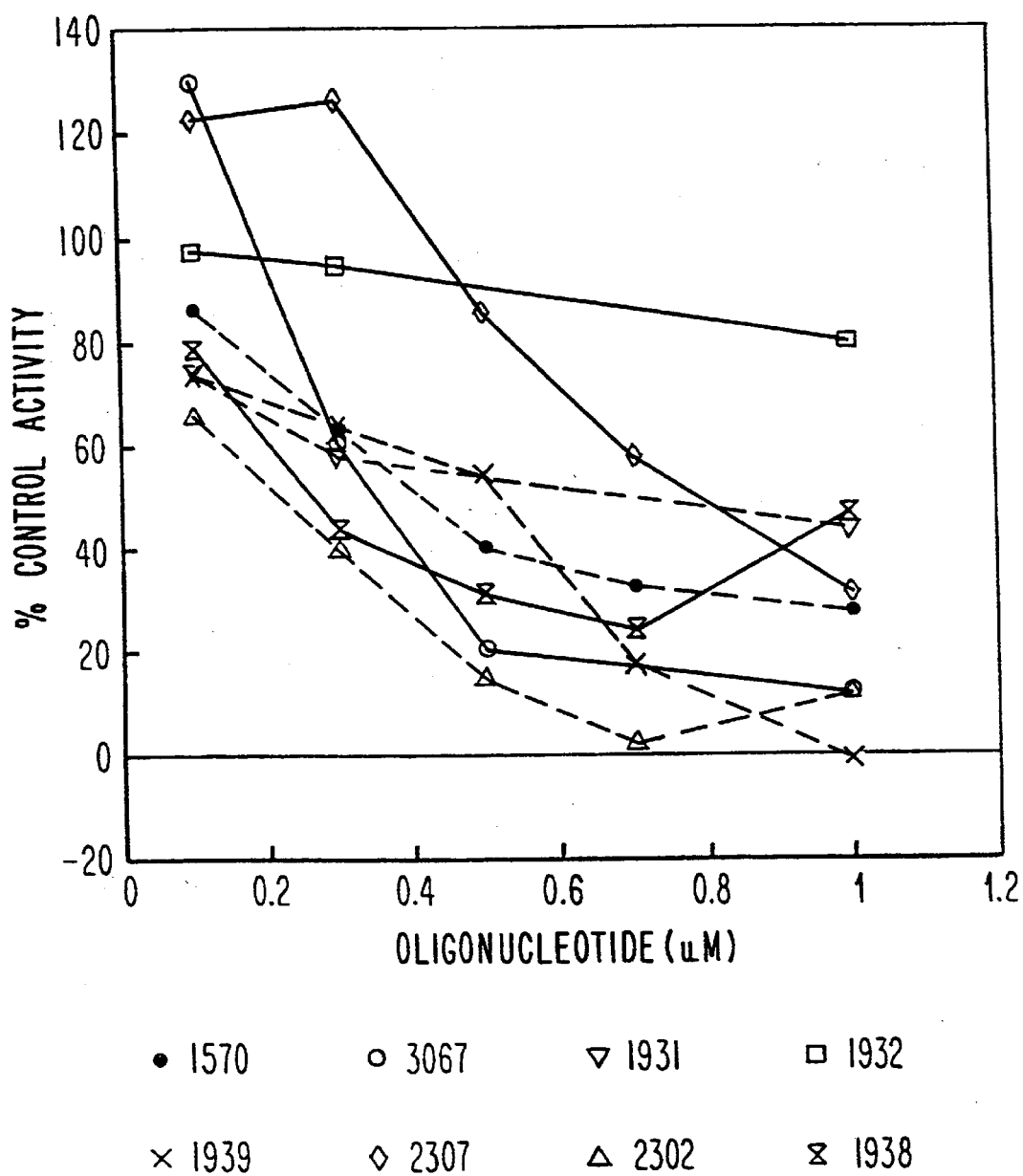
FIG. 8 is a graphical representation of the effects of selected antisense oligonucleotides on ICAM-1 expression in A549 human lung carcinoma cells.

Based on the initial data obtained with the five original targets, additional oligonucleotides were designed which would hybridize with the ICAM-1 mRNA. The antisense oligonucleotide (ISIS 3067) which hybridizes to the predicted transcription initiation site (5' cap site) was approximately as active in IL-1β-stimulated cells as the oligonucleotide that hybridizes to the AUG codon (ISIS 1570), as shown in FIG. 8. ISIS 1931 and 1932 hybridize 5' and 3', respectively, to the AUG translation initiation codon. All three oligonucleotides that hybridize to the AUG region inhibit ICAM-1 expression, though ISIS 1932 was slightly less active than ISIS 1570 and ISIS 1931. Oligonucleotides which hybridize to the coding region of ICAM-1 mRNA (ISIS 1933, 1934, 1935, 1574 and 1936) exhibited weak activity. Oligonucleotides that hybridize to the translation termination codon (ISIS 1937 and 1938) exhibited moderate activity.

Surprisingly, the most active antisense oligonucleotide was ISIS 1939, a phosphorothioate oligonucleotide targeted to a sequence in the 3'-untranslated region of ICAM-1 mRNA (see Table 1). Other oligonucleotides having the same sequence were tested, 2'-O-methyl (ISIS 2973) and 2'-fluoro (ISIS 2637); however, they did not exhibit this level of activity. Oligonucleotides targeted to other 3' untranslated sequences (ISIS 1572, 1573 and 1940) were also not as active as ISIS-1939. In fact, ISIS 1940, targeted to the polyadenylation signal, did not inhibit ICAM-1 expression.

Because ISIS 1939 proved unexpectedly to exhibit the greatest antisense activity of the original 16 oligonucleotides tested, other oligonucleotides were designed to hybridize to sequences in the 3'-untranslated region of ICAM-1 mRNA (ISIS 2302, 2303, 2304, 2305, and 2307, as shown in Table 1). ISIS 2307, which hybridizes to a site only five bases 3' to the ISIS 1939 target, was the least active of the series (FIG. 8). ISIS 2302, which hybridizes to the ICAM-1 mRNA at a position 143 bases 3' to the ISIS 1939 target, was the most active of the series, with activity comparable to that of ISIS 1939. Examination of the predicted RNA secondary structure of the human ICAM-1 mRNA 3'-untranslated region (according to M. Zuker, Science 1989, 244, 48–52) revealed that both ISIS 1939 and ISIS 2302 hybridize to sequences predicted to be in a stable stem-loop structure. Current dogma suggests that regions of RNA secondary structure should be avoided when designing antisense oligonucleotides. Thus, ISIS 1939 and ISIS 2302 would not have been predicted to inhibit ICAM-1 expression.

The control oligonucleotide ISIS 1821 did inhibit ICAM-1 expression in HUVEC cells with activity comparable to that of ISIS 1934; however, in A549 cells ISIS 1821 was less effective than ISIS 1934. The negative control, ISIS 1821, was found to have a small amount of activity against ICAM expression, probably due in part to its ability to hybridize (12 of 13 base match) to the ICAM-1 mRNA at a position 15 bases 3' to the AUG translation initiation codon.

These studies indicate that the AUG translation initiation codon and specific 3'-untranslated sequences in the ICAM-1 mRNA were the most susceptible to antisense oligonucleotide inhibition of ICAM-1 expression.

Figure 9:
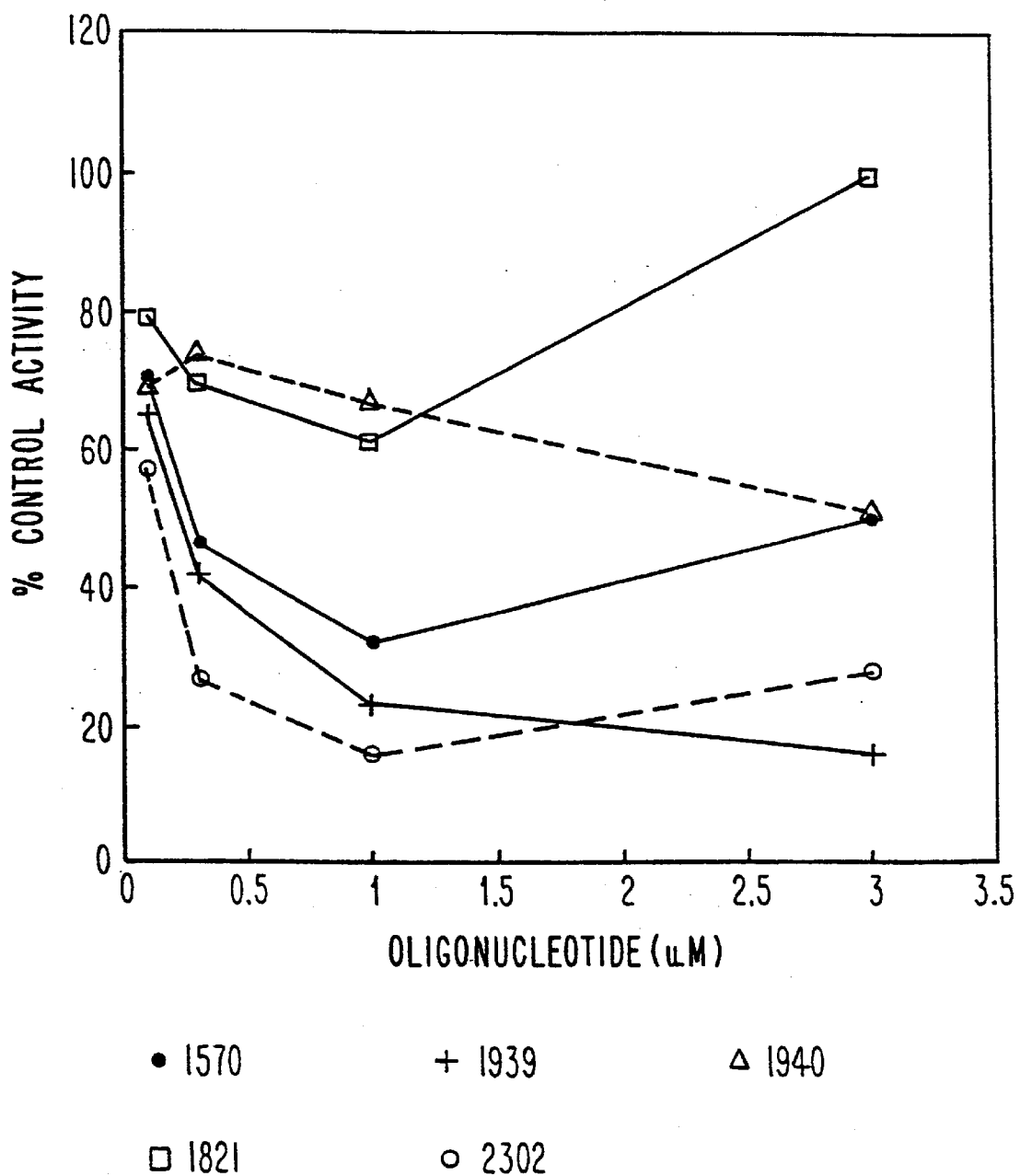
FIG. 9 is a graphical representation of the effects of selected antisense oligonucleotides on ICAM-1 expression in primary human keratinocytes.

In addition to inhibiting ICAM-1 expression in human umbilical vein cells and the human lung carcinoma cells (A549), ISIS 1570, ISIS 1939 and ISIS 2302 were shown to inhibit ICAM-1 expression in the human epidermal carcinoma A431 cells and in primary human keratinocytes (shown in FIG. 9). These data demonstrate that antisense oligonucleotides are capable of inhibiting ICAM-1 expression in several human cell lines. Furthermore, the rank order potency of the oligonucleotides is the same in the four cell lines examined. The fact that ICAM-1 expression could be inhibited in primary human keratinocytes is important because epidermal keratinocytes are an intended target of the antisense nucleotides.

Example 6

Antisense Oligonucleotide Inhibition of ICAM-1 Expression in Cells Stimulated with other Cytokines Two oligonucleotides, ISIS 1570 and ISIS 1939, were tested for their ability to inhibit TNF-α and IFN-γ-induced ICAM-1 expression. Treatment of A549 cells with 1 μM antisense oligonucleotide inhibited IL-1β, TNF-α and IFN-γ-induced ICAM-1 expression in a sequence-specific manner. The antisense oligonucleotides inhibited IL-1β and TNF-α-induced ICAM-1 expression to a similar extent, while IFN-γ-induced ICAM-1 expression was more sensitive to antisense inhibition. The control oligonucleotide, ISIS 2821, did not significantly inhibit IL-1β- or TNF-α-induced ICAM-1 expression and inhibited IFN-γ-induced ICAM-1 expression slightly, as follows:

| Cytokine | Antisense Oligonucleotide (% Control Expression) | | |
|---|---|---|---|
| | ISIS 1570 | ISIS 1939 | ISIS 1821 |
| 3 U/ml IL-1β | 56.6 ± 2.9 | 38.1 ± 3.2 | 95 ± 6.6 |
| 1 ng/ml TNF-α | 58.1 ± 0.9 | 37.6 ± 4.1 | 103.5 ± 8.2 |
| 100 U/ml gamma-IFN | 38.9 ± 3.0 | 18.3 ± 7.0 | 83.0 ± 3.5 |

Example 7

Antisense Effects are Abolished by Sense Strand Controls

The antisense oligonucleotide inhibition of ICAM-1 expression by the oligonucleotides ISIS 1570 and ISIS 1939 could be reversed by hybridization of the oligonucleotides with their respective sense strands. The phosphorothioate sense strand for ISIS 1570 (ISIS 1575), when applied alone, slightly enhanced IL-1β-induced ICAM-1 expression. Premixing ISIS 1570 with ISIS 1575 at equal molar concentrations, prior to addition to the cells, blocked the effects of ISIS 1570. The complement to ISIS 1939 (ISIS 2115) enhanced ICAM-1 expression by 46% when added to the cells alone. Prehybridization of ISIS 2115 to ISIS 1939 completely blocked the inhibition of ICAM-1 expression by ISIS 1939.

Example 8

Measurement of Oligonucleotide Tm (Dissociation Temperature of Oligonucleotide from Target)

To determine if the potency of the inhibition of ICAM-1 expression by antisense oligonucleotides was due to their affinity for their target sites, thermodynamic measurements were made for each of the oligonucleotides. The antisense oligonucleotides (synthesized as phosphorothioates) were hybridized to their complementary DNA sequences (synthesized as phosphodiesters). Absorbance vs. temperature profiles were measured at 4 μM each strand oligonucleotide in 100 mM Na+, 10 mM phosphate, 0.1 mM EDTA, pH7.0. Tm's and free energies of duplex formation were obtained from fits of data to a two-state model with linear sloping baselines (Petersheim, M. and D. H. Turner, *Biochemistry* 1983, 22, 256–263). Results are averages of at least three experiments.

When the antisense oligonucleotides were hybridized to their complementary DNA sequences (synthesized as phosphodiesters), all of the antisense oligonucleotides with the exception of ISIS 1940 exhibited a Tm of at least 50° C. All the oligonucleotides should therefore be capable of hybridizing to the target ICAM-1 mRNA if the target sequences were exposed. Surprisingly, the potency of the antisense oligonucleotide did not correlate directly with either Tm or ΔG°$_{37}$. The oligonucleotide with the greatest biological activity, ISIS 1939, exhibited a Tm which was lower than that of the majority of the other oligonucleotides. Thus, hybridization affinity is not sufficient to ensure biological activity.

Example 9

Effect of Oligonucleotide Length on Antisense Inhibition of ICAM-1 Expression

Figure 10:
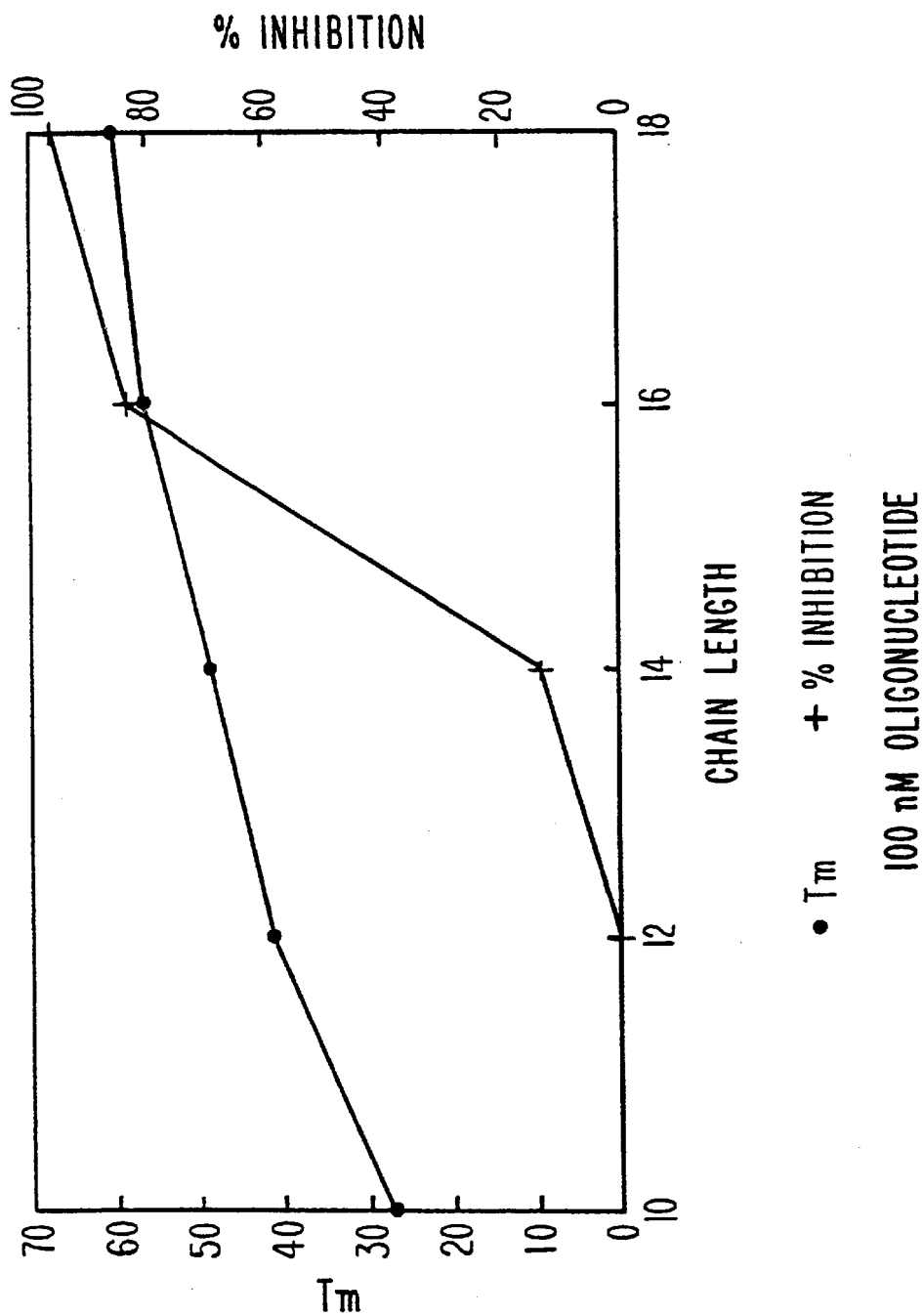
FIG. 10 is a graphical representation of the relationship between oligonucleotide chain length, Tm and effect on inhibition of ICAM-1 expression.

The effect of oligonucleotide length on antisense activity was tested using truncated versions of ISIS 1570 (ISIS 2165, 2173, 2149, 2163 and 2164) and ISIS 1939 (ISIS 2540, 2544, 2545, 2546, 2547 and 2548). In general, antisense activity decreased as the length of the oligonucleotides decreased. Oligonucleotides 16 bases in length exhibited activity slightly less than 18 base oligonucleotides. Oligonucleotides 14 bases in length exhibited significantly less activity, and oligonucleotides 12 or 10 bases in length exhibited only weak activity. Examination of the relationship between oligonucleotide length and Tm and antisense activity reveals that a sharp transition occurs between 14 and 16 bases in length, while Tm increases linearly with length (FIG. 10).

Example 10

Specificity of Antisense Inhibition of ICAM-1

The specificity of the antisense oligonucleotides ISIS 1570 and ISIS 1939 for ICAM-1 was evaluated by immunoprecipitation of $^{35}$S-labelled proteins. A549 cells were grown to confluence in 25 cm$^2$ tissue culture flasks and treated with antisense oligonucleotides as described in Example 4. The cells were stimulated with interleukin-1β for 14 hours, washed with methionine-free DMEM plus 10% dialyzed fetal calf serum, and incubated for 1 hour in methionine-free medium containing 10% dialyzed fetal calf serum, 1 μM oligonucleotide and interleukin-1β as indicated. $^{35}$S-Methionine/cysteine mixture (Tran$^{35}$S-label, purchased from ICN, Costa Mesa, Calif.) was added to the cells to an activity of 100 μCi/ml and the cells were incubated an additional 2 hours. Cellular proteins were extracted by incubation with 50 mM Tris-HCl pH 8.0, 150 mM NaCl, 1.0% NP-40, 0.5% deoxycholate and 2 mM EDTA (0.5 ml per well) at 4° C. for 30 minutes. The extracts were clarified by centrifugation at 18,000×g for 20 minutes. The supernatants were preadsorbed with 200 μl protein G-Sepharose beads (Bethesda Research Labs, Bethesda Md.) for 2 hours at 4° C., divided equally and incubated with either 5 μg ICAM-1 monoclonal antibody (purchased from AMAC Inc., Westbrook Me.) or HLA-A,B antibody (W6/32, produced by murine hybridoma cells obtained from the American Type Culture Collection, Bethesda, Md.) for 15 hours at 4° C. Immune complexes were trapped by incubation with 200 μl of a 50% suspension of protein G-Sepharose (v/v) for 2 hours at 4° C., washed 5 times with lysis buffer and resolved on an SDS-polyacrylamide gel. Proteins were detected by autoradiography.

Treatment of A549 cells with 5 units/ml of interleukin-1β was shown to result in the synthesis of a 95–100 kDa protein migrating as a doublet which was immunoprecipitated with the monoclonal antibody to ICAM-1. The appearance as a doublet is believed to be due to differently glycosylated forms of ICAM-1. Pretreatment of the cells with the antisense oligonucleotide ISIS 1570 at a concentration of 1 μM decreased the synthesis of ICAM-1 by approximately 50%, while 1 μM ISIS 1939 decreased ICAM-1 synthesis to near background. Antisense oligonucleotide ISIS 1940, inactive in the ICAM-1 ELISA assay (Examples 1 and 5) did not significantly reduce ICAM-1 synthesis. None of the antisense oligonucleotides hybridizable with ICAM-1 targets had a demonstrable effect on HLA-A, B synthesis, demonstrating the specificity of the oligonucleotides for ICAM-1. Furthermore, the proteins which nonspecifically precipitated with the ICAM-1 antibody and protein G-Sepharose were not significantly affected by treatment with the antisense oligonucleotides.

Example 11

Figure 11:
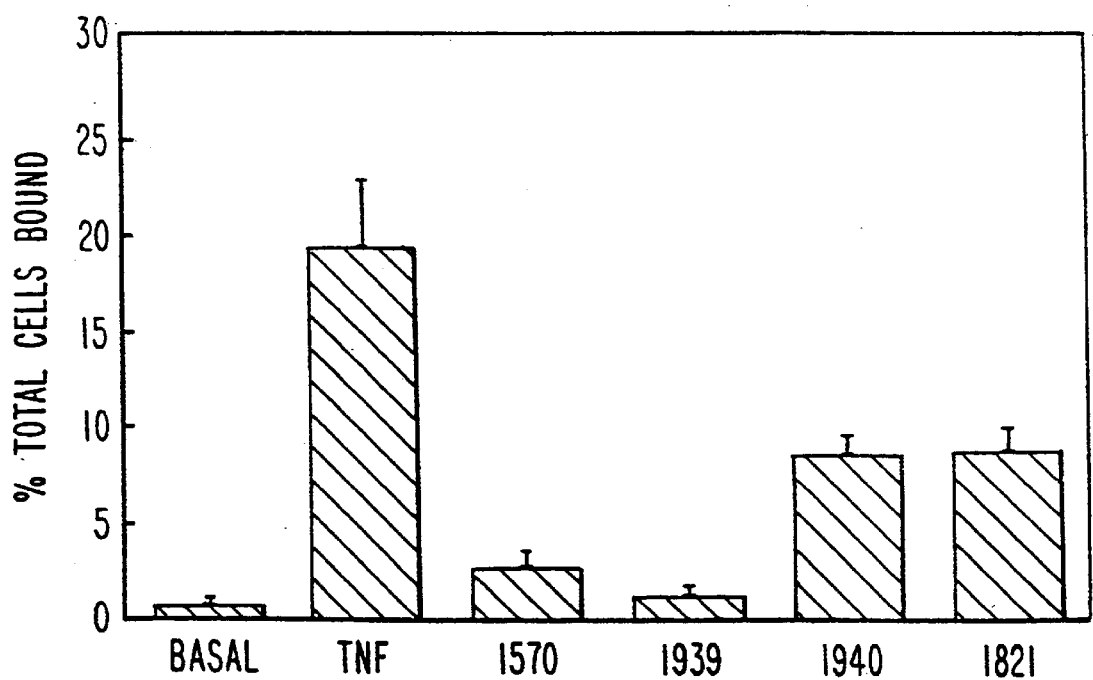
FIG. 11 is a graphical representation of the effect of selected antisense oligonucleotides on ICAM-1 mediated adhesion of DMSO differentiated HL-60 cells to control and tumor necrosis factor treated human umbilical vein endothelial cells.

Screening of Additional Antisense Oligonucleotides for Activity Against ICAM-1 by Cell Adhesion Assay Human umbilical vein endothelial (HUVEC) cells were grown and treated with oligonucleotides as in Example 4. Cells were treated with either ISIS 1939, ISIS 1940, or the control oligonucleotide ISIS 1821 for 4 hours, then stimulated with TNF-α for 20 hours. Basal HUVEC minimally bound HL-60 cells, while TNF-stimulated HUVEC bound 19% of the total cells added. Pretreatment of the HUVEC monolayer with 0.3 μM ISIS 1939 reduced the adherence of HL-60 cells to basal levels, as shown in FIG. 11. The control oligonucleotide, ISIS 1821, and ISIS 1940 reduced the percentage of cells adhering from 19% to 9%. These data indicate that antisense oligonucleotides targeting ICAM-1 may specifically decrease adherence of a leukocyte-like cell line (HL-60) to TNF-α-treated HUVEC.

Example 12

ELISA Screening of Antisense Oligonucleotides for Activity Against ELAM-1 Gene Expression Primary human umbilical vein endothelial (HUVEC) cells, passage 2 to 5, were plated in 96-well plates and allowed to reach confluence. Cells were washed three times with Opti-MEM (GIECO, Grand Island N.Y.). Cells were treated with increasing concentrations of oligonucleotide diluted in Opti-MEM containing 10 μg/ml DOTMA solution (Bethesda Research Labs, Bethesda Md.) for 4 hours at 37° C. The medium was removed and replaced with EGM-UV (Clonetics, San Diego Calif.) plus oligonucleotide. Tumor necrosis factor α was added to the medium (2.5 ng/ml) and the cells were incubated an additional 4 hours at 37° C.

ELAM-1 expression was determined by ELISA. Cells were gently washed three times with Dulbecco's phosphate-buffered saline (D-PBS) prewarmed to 37° C. Cells were fixed with 95% ethanol at 4° C. for 20 minutes, washed three times with D-PBS and blocked with 2% BSA in D-PBS. Cells were incubated with ELAM-1 monoclonal antibody BBA-1 (R&D Systems, Minneapolis Minn.) diluted to 0.5 μg/ml in D-PBS containing 2% BSA for 1 hour at 37° C. Cells were washed three times with D-PBS and the bound ELAM-1 antibody detected with biotinylated goat anti-mouse secondary antibody followed by β-galactosidase-conjugated streptavidin as described in Example 1.

The activity of antisense phosphorothioate oligonucleotides which target 11 different regions on the ELAM-1 cDNA and two oligonucleotides which target ICAM-1 (as controls) was determined using the ELAM-1 ELISA. The oligonucleotide and targets are shown in Table 2.

TABLE 2

ANTISENSE OLIGONUCLEOTIDES WHICH TARGET HUMAN ELAM-1

| ISIS NO. | SEQ ID NO. | TARGET REGION | MODIFICATION |
|---|---|---|---|
| 1926 | 28 | AUG Codon (143–164) | P = S |
| 2670 | 29 | 3'-Untranslated (3718–3737) | P = S |
| 2673 | 30 | 3'-Untranslated (2657–2677) | P = S |
| 2674 | 31 | 3'-Untranslated (2617–2637) | P = S |
| 2678 | 32 | 3'-Untranslated (3558–3577) | P = S |
| 2679 | 33 | 5'-Untranslated (41–60) | P = S |
| 2680 | 34 | 3'-Untranslated (3715–3729) | P = S |
| 2683 | 35 | AUG Codon (143–163) | P = S |
| 2686 | 36 | AUG Codon (149–169) | P = S |
| 2687 | 37 | 5'-Untranslated (18–37) | P = S |
| 2693 | 38 | 3'-Untranslated (2760–2788) | P = S |
| 2694 | 39 | 3'-Untranslated (2934–2954) | P = S |

Figure 12:
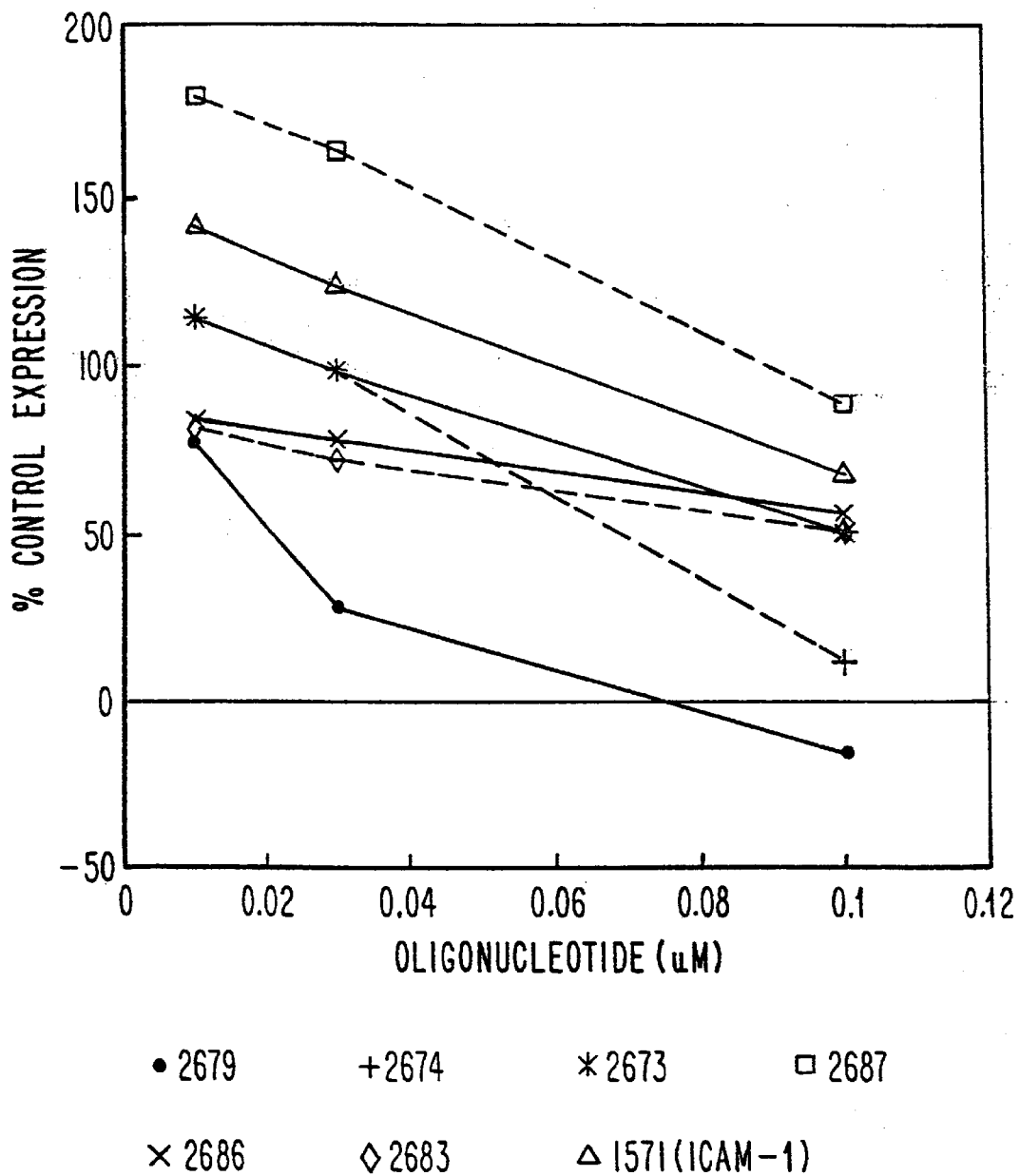
FIG. 12 is a graphical representation of the effects of selected antisense oligonucleotides on ELAM-1 expression on tumor necrosis factor-treated human umbilical vein endothelial cells.

In contrast to what was observed with antisense oligonucleotides targeted to ICAM-1 (Example 5), the most potent oligonucleotide modulator of ELAM-1 activity (ISIS 2679) was hybridizable with specific sequences in the 5'-untranslated region of ELAM-1. ISIS 2687, an oligonucleotide which hybridized to sequences ending three bases upstream of the ISIS 2679 target, did not show significant activity (FIG. 12). Therefore, ISIS 2679 hybridizes to a unique site on the ELAM-1 mRNA, which is uniquely sensitive to inhibition with antisense oligonucleotides. The sensitivity of this site to inhibition with antisense oligonucleotides was not predictable based upon RNA secondary structure predictions or information in the literature.

Example 13

Figure 13:
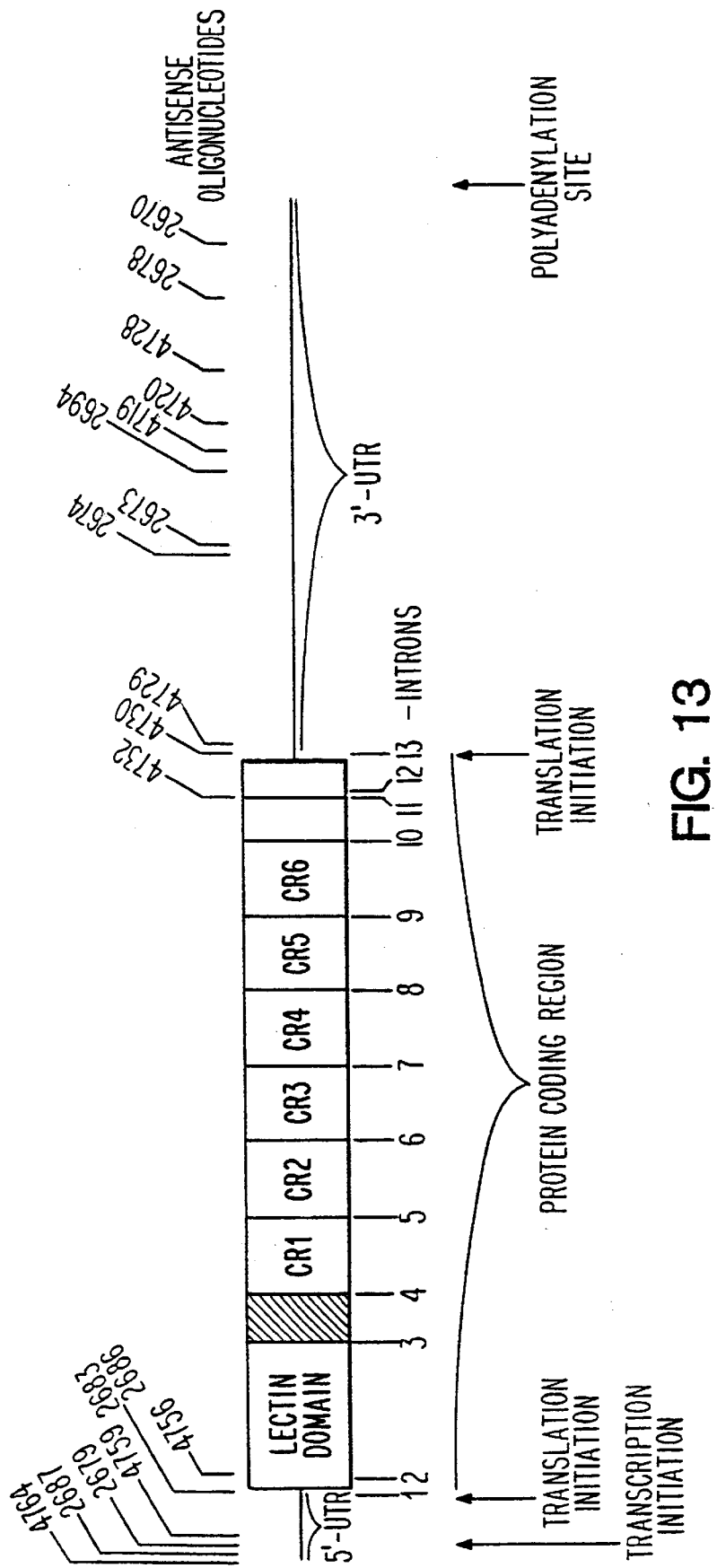
FIG. 13 is a graphical representation of the human ELAM-1 mRNA showing target sites of antisense oligonucleotides.

ELISA Screening of Additional Antisense Oligonucleotides for Activity Against ELAM-1 Gene Expression Inhibition of ELAM-1 expression by eighteen antisense phosphorothioate oligonucleotides was determined using the ELISA assay as described in Example 12. The target sites of these oligonucleotides on the ELAM-1 mRNA are shown in FIG. 13. The sequence and activity of each oligonucleotide against ELAM-1 are shown in Table 3. The oligonucleotides indicated by an asterisk (*) have IC50's of approximately 50 nM or below and are preferred. IC50 indicates the dosage of oligonucleotide which results in 50% inhibition of ELAM-1 expression.

TABLE 3

Inhibition of human ELAM-1 expression by antisense oligonucleotides
ELAM-1 expression is given as % of control

| ISIS# | SEQ ID NO: | POSITION | | SEQUENCE | VCAM-1 EXPRESSION | |
|---|---|---|---|---|---|---|
| | | | | | 30 nM oligo | 50 nM oligo |
| *4764 | 52 | 5'-UTR | 1–19 | GAAGTCAGCCAAGAACAGCT | 70.2 | 50.2 |
| 2687 | 37 | 5'-UTR | 17–36 | TATAGGAGTTTTGATGTGAA | 91.1 | 73.8 |
| *2679 | 33 | 5'-UTR | 40–59 | CTGCTGCCTCTGTCTCAGGT | 6.4 | 6.0 |
| *4759 | 53 | 5'-UTR | 64–83 | ACAGGATCTCTCAGGTGGGT | 30.0 | 20.2 |
| *2683 | 35 | AUG | 143–163 | AATCATGACTTCAAGAGTTCT | 47.9 | 48.5 |
| *2686 | 36 | AUG | 148–168 | TGAAGCAATCATGACTTCAAG | 51.1 | 46.9 |
| *4756 | 54 | I/E | 177–196 | CCAAAGTGAGAGCTGAGAGA | 53.9 | 35.7 |
| 4732 | 55 | Coding | 1936–1955 | CTGATTCAAGGCTTTGGCAG | 68.5 | 55.3 |
| *4730 | 56 | I/E 3'UTR | 2006–2025 | TTCCCCAGATGCACCTGTTT | 14.1 | 2.3 |
| *4729 | 57 | 3'-UTR | 2063–2082 | GGGCCAGAGACCCGAGGAGA | 49.4 | 46.3 |
| *2674 | 31 | 3'-UTR | 2617–2637 | CACAATCCTTAAGAACTCTTT | 33.5 | 28.1 |
| 2673 | 30 | 3'-UTR | 2656–2676 | GTATGGAAGATTATAATATAT | 58.9 | 53.8 |
| 2694 | 39 | 3'-UTR | 2933–2953 | GACAATATACAAACCTTCCAT | 72.0 | 64.6 |
| *4719 | 58 | 3'-UTR | 2993–3012 | ACGTTTGGCCTCATGGAAGT | 36.8 | 34.7 |
| 4720 | 59 | 3'-UTR | 3093–3112 | GGAATGCAAAGCACATCCAT | 63.5 | 70.6 |
| *2678 | 32 | 3'-UTR | 3557–3576 | ACCTCTGCTGTTCTGATCCT | 24.9 | 15.3 |
| 2670 | 29 | 3'-UTR | 3717–3736 | ACCACACTGGTATTTCACAC | 72.2 | 67.2 |

I/E indicates Intron/Exon junction
oligonucleotides with IC50's of approximately 50 nM or below are indicated by an asterisk (*)

An additional oligonucleotide targeted to the 3'-untranslated region (ISIS 4728) did not inhibit ELAM expression.

Example 14

Figure 14:
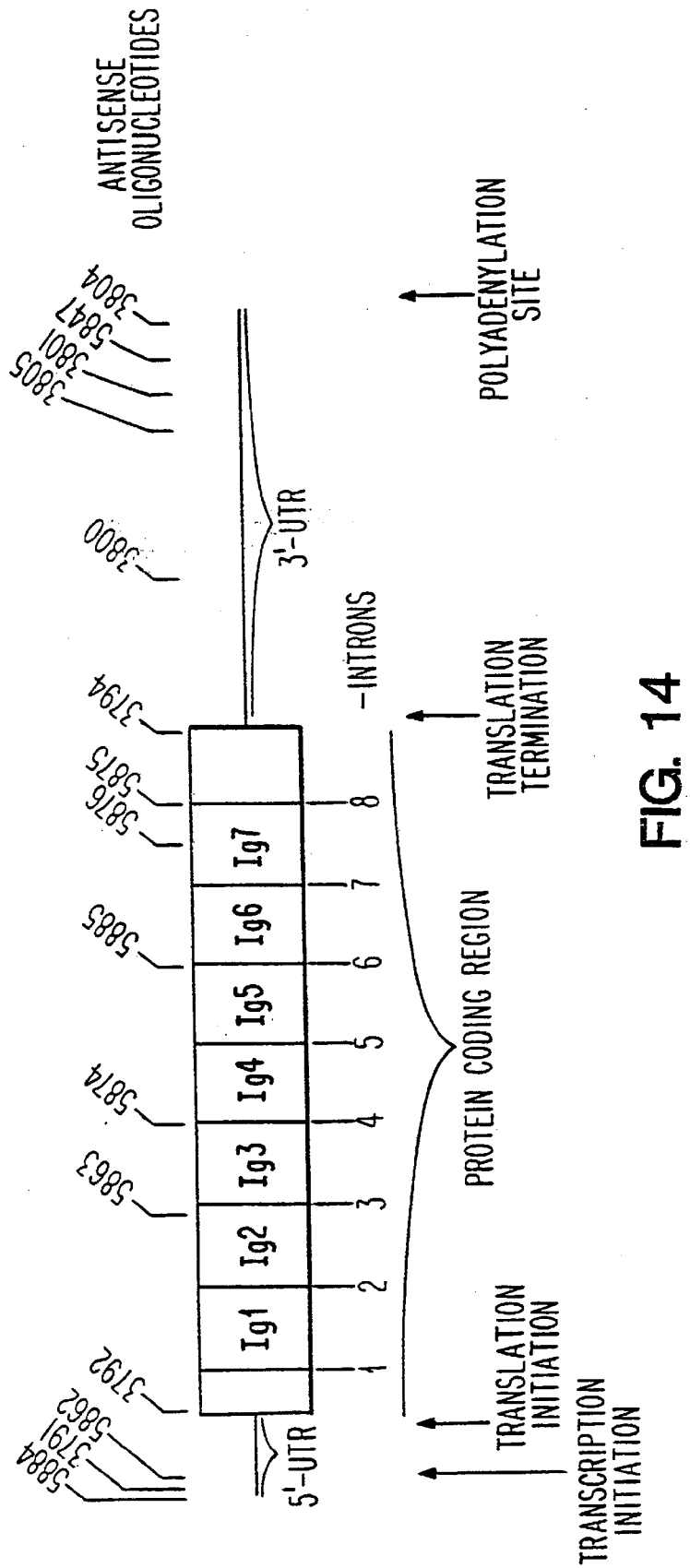
FIG. 14 is a graphical representation of the human VCAM-1 mRNA showing target sites of antisense oligonucleotides.

ELISA Screening of Antisense Oligonucleotides for Activity Against VCAM-1 Gene Expression Inhibition of VCAM-1 expression by fifteen antisense phosphorothioate oligonucleotides was determined using the ELISA assay approximately as described in Example 12, except that cells were stimulated with TNF-α for 16 hours and VCAM-1 expression was detected by a VCAM-1 specific monoclonal antibody (R & D Systems, Minneapolis, Minn.) used at 0.5 μg/ml. The target sites of these oligonucleotides on the VCAM-1 mRNA are shown in FIG. 14. The sequence and activity of each oligonucleotide against VCAM-1 are shown in Table 4. The oligonucleotides indicated by an asterisk (*) have IC50's of approximately 50 nM or below and are preferred. IC50 indicates the dosage of oligonucleotide which results in 50% inhibition of VCAM-1 expression.

TABLE 4

Inhibition of human VCAM-1 expression by antisense oligonucleotides
VCAM-1 expression is given as % of control

| ISIS# | SEQ ID NO: | POSITION | | SEQUENCE | VCAM-1 EXPRESSION | |
|---|---|---|---|---|---|---|
| | | | | | 30 nM oligo | 50 nM oligo |
| *5884 | 60 | 5'-UTR | 1–19 | CGATGCAGATACCGCGGAGT | 79.2 | 37.2 |
| 3791 | 61 | 5'-UTR | 38–58 | GCCTGGGAGGGTATTCAGCT | 92.6 | 58.0 |
| 5862 | 62 | 5'-UTR | 48–68 | CCTGTGTGTGCCTGGGAGGG | 115.0 | 83.5 |
| *3792 | 63 | AUG | 110–129 | GGCATTTTAAGTTGCTGTCG | 68.7 | 33.7 |
| 5863 | 64 | CODING | 745–764 | CAGCCTGCCTTACTGTGGGC | 95.8 | 66.7 |
| *5874 | 65 | CODING | 1032–1052 | CTTGAACAATTAATTCCACCT | 66.5 | 35.3 |
| 5885 | 66 | E/I | 1633–1649 + intron | TTACCATTGACATAAAGTGTT | 84.4 | 52.4 |
| *5876 | 67 | CODING | 2038–2057 | CTGTGTCTCCTGTCTCCGCT | 43.5 | 26.6 |
| *5875 | 68 | CODING | 2183–2203 | GTCTTTGTTGTTTCTCTTCC | 59.2 | 34.8 |
| 3794 | 69 | TERMIN. | 2344–2362 | TGAACATATCAAGCATTAGC | 75.3 | 52.6 |
| *3800 | 70 | 3'-UTR | 2620–2639 | GCAATCTTGCTATGGCATAA | 64.4 | 47.7 |
| *3805 | 71 | 3'-UTR | 2826–2845 | CCCGGCATCTTTACAAAACC | 67.7 | 44.9 |
| *3801 | 50 | 3'-UTR | 2872–2892 | AACCCAGTGCTCCCTTTGCT | 36.5 | 21.3 |
| *5847 | 72 | 3'-UTR | 2957–2976 | AACATCTCCGTACCATGCCA | 51.8 | 24.6 |
| *3804 | 51 | 3'-UTR | 3005–3024 | GGCCACATTGGGAAAGTTGC | 55.1 | 29.3 |

E/I indicates excn/intron junction
Oligonucleotides with IC50's of approximately 50 nM or below are indicated by an asterisk (*).

Example 15

ICAM-1 Expression in C8161 Human Melanoma Cells

Human melanoma cell Line C8161 (a gift of Dr. Dan Welch, Hershey Medical Center) was derived from an abdominal wall metastasis from a patient with recurrent malignant melanoma. These cells form multiple metastases in lung, subcutis, spleen, liver and regional lymph nodes after subcutaneous, intradermal and intravenous injection into athymic nude mice. Cells were grown in DMA-F12 medium containing 10% fetal calf serum and were passaged using 2 mM EDTA.

Exposure of C8161 cells to TNF-α resulted in a six-fold increase in cell surface expression of ICAM-1 and an increase in ICAM-1 mRNA levels in these cells. ICAM-1 expression on the cell surface was measured by ELISA. Cells were treated with increasing concentrations of antisense oligonucleotides in the presence of 15 μg/ml Lipofectin for 4 hours at 37° C. ICAM-1 expression was induced by incubation with 5 ng/ml TNF-α for 16 hours. Cells were washed 3× in DPBS and fixed for 20 minutes in 2% formaldehyde. Cells were washed in DPBS, blocked with 2% BSA for 1 hour at 37° C. and incubated with ICAM-1 monoclonal antibody 84H10 (AMAC, Inc., Westbrooke, Me.). Detection of bound antibody was determined by incubation with a biotinylated goat anti-mouse IgG followed by incubation with β-galactosidase-conjugated streptavidin and developed with chlorophenol red-β-D-galactopyranoside and quantified by absorbance at 575 nm. ICAM-1 mRNA levels were measured by Northern blot analysis.

Example 16

Oligonucleotide Inhibition of ICAM-1 Expression in C8161 Human Melanoma Cells

Figure 15:
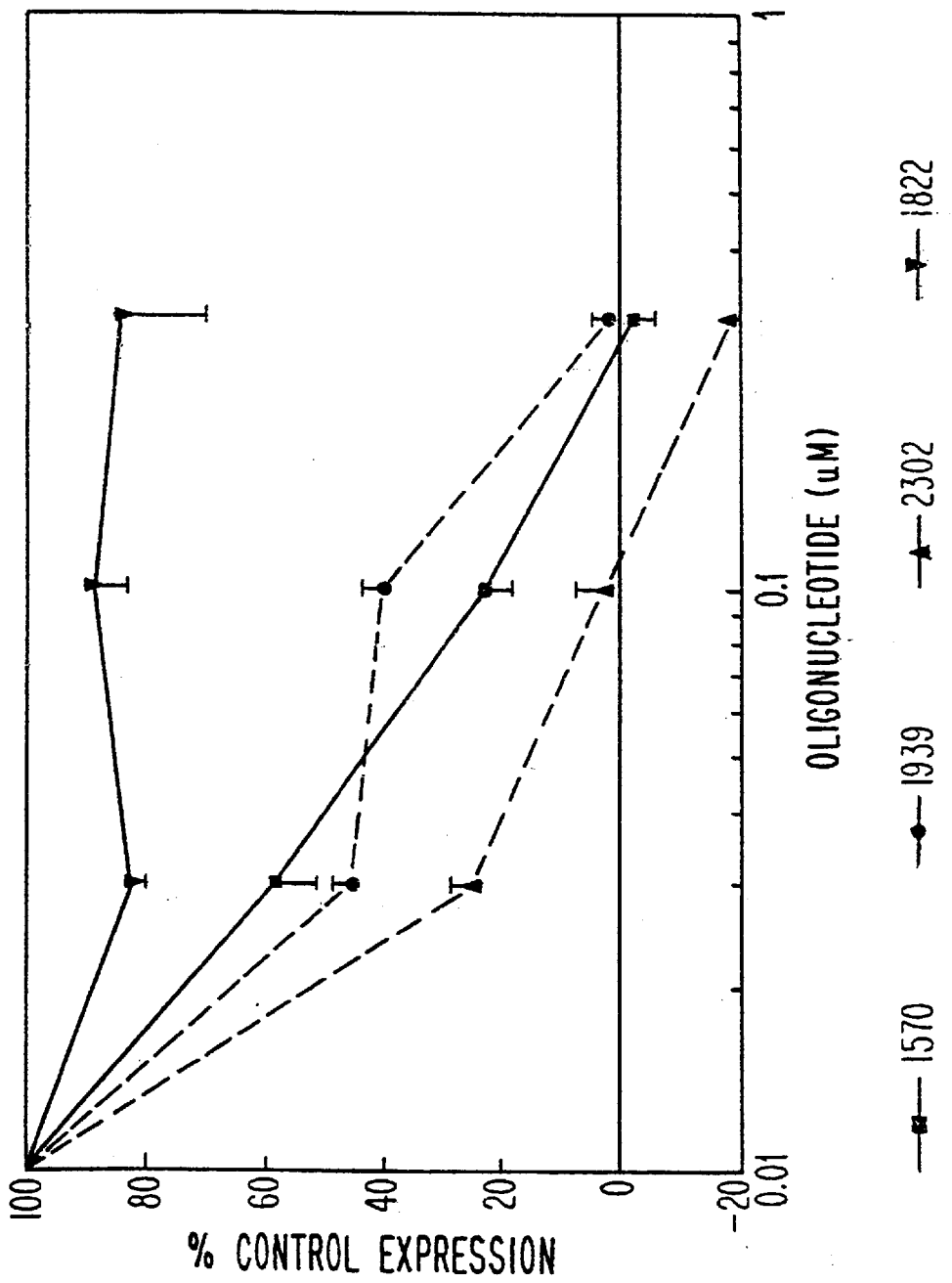
FIG. 15 is a line graph showing inhibition of ICAM-1 expression in C8161 human melanoma cells following treatment with antisense oligonucleotides complementary to ICAM-1.

As shown in FIG. 15, antisense oligonucleotides ICAM 1570 (SEQ ID NO: 1), ISIS 1939 (SEQ ID NO: 15) and ISIS 2302 (SEQ ID NO: 22) targeted to ICAM-1 decreased cell surface expression of ICAM-1 (detected by ELISA as in Example 16). ISIS 1822, a negative control oligonucleotide complementary to 5-lipoxygenase, did not affect ICAM-1 expression. The data were expressed as percentage of control activity, calculated as follows: (ICAM-1 expression for oligonucleotide-treated, cytokine-induced cells)—(basal ICAM-1 expression)/(ICAM-1 cytokine-induced expression)—(basal ICAM-1 expression)×100.

ISIS 1939 (SEQ ID NO: 15) and ISIS 2302 (SEQ ID NO: 22) markedly reduced ICAM-1 mRNA levels (detected by Northern blot analysis), but ISIS-1570 (SEQ ID NO: 1) decreased ICAM-1 mRNA levels only slightly.

Example 17

Experimental Metastasis Assay

To evaluate the role of ICAM-1 in metastasis, experimental metastasis assays were performed by injecting 1×10⁵ C8161 cells into the lateral tail vein of athymic nude mice. Treatment of C8161 cells with the cytokine TNF-α and interferon γ has previously been shown to result in an increased number of lung metastases when cells were injected into nude mice [Miller, D. E. and Welch, D. R., Proc. Am. Assoc. Cancer Res. 1990, 13, 353].

After 4 weeks, mice were sacrificed, organs were fixed in Bouin's fixative and metastatic lesions on lungs were scored with the aid of a dissecting microscope. Four-week-old female athymic nude mice (Harlan Sprague Dawley) were used. Animals were maintained under the guidelines of the NIH. Groups of 4–8 mice each were tested in experimental metastasis assays.

Example 18

Antisense Oligonucleotides ISIS 1570 and ISIS 2302 Decrease Metastatic Potential of C8161 Cells Treatment of C8161 cells with antisense oligonucleotides ISIS 1570 and ISIS 2302, complementary to ICAM-1, was performed in the presence of the cationic lipid, Lipofectin (Gibco/BRL, Gaithersburg, Md.). Antisense oligonucleotides were synthesized as described in Example 3. Cells were seeded in 60 mm tissue culture dishes at 10⁶ cells/ml and incubated at 37° C. for 3 days, washed with Opti-MEM (Gibco/BRL) 3 times and 100 μl of Opti-MEM medium was added to each well. 0.5 μM oligonucleotide and 15 μg/ml lipofectin were mixed at room temperature for 15 minutes. 25 μl of the oligonucleotide-lipofectin mixture was added to the appropriate dishes and incubated at 37° C. for 4 hours. The oligonucleotide-lipofectin mixture was removed and replaced with DME-F12 medium containing 10% fetal calf serum. After 4 hours, 500 U/ml TNF-α was added to the appropriate wells and incubated for 18 hours at which time cells were removed from the plates, counted and injected into athymic nude mice.

Treatment of C8161 cells with ISIS 1570 (SEQ ID NO: 1) or ISIS 2302 (SEQ ID NO: 22) decreased the metastatic potential of these cells, and eliminated the enhanced metastatic ability of C8161 which resulted from TNF-α treatment. Data are shown in Table 5.

TABLE 5

Effect of antisense oligonucleotides to ICAM-1 on experimental metastasis of human melanoma cell line C8161

| Treatment | No. Lung Metastases per Mouse (Mean ± S.E.M.) |
|---|---|
| Lipofectin only | 64 ± 13 |
| Lipofectin + TNF-α | 81 ± 8 |
| ISIS-1570 + Lipofectin | 38 ± 15 |
| ISIS-2302 + Lipofectin | 23 ± 6 |
| ISIS-1570 + Lipofectin + TNF-α | 49 ± 6 |
| ISIS-2302 + Lipofectin + TNF-α | 31 ± 8 |

Example 19

Murine Models for Testing Antisense Oligonucleotides Against ICAM-1

Many conditions which are believed to be mediated by intercellular adhesion molecules are not amenable to study in humans. For example, allograft rejection is a condition which is likely to be ameliorated by interference with ICAM-1 expression, but clearly this must be evaluated in animals rather than human transplant patients. Another such example is inflammatory bowel disease, and yet another is neutrophil migration (infiltration). These conditions can be tested in animal models, however, such as the mouse models used here.

Oligonucleotide sequences for inhibiting ICAM-1 expression in murine cells were identified. Murine ICAM-1 has approximately 50% homology with the human ICAM-1 sequence; a series of oligonucleotides which target the mouse ICAM-1 mRNA sequence were designed and synthesized, using information gained from evaluation of oligonucleotides targeted to human ICAM-1. These oligonucleotides were screened for activity using an immunoprecipitation assay.

Murine DCEK-ICAM-1 cells (a gift from Dr. Adrienne Brian, University of California at San Diego) were treated with 1 μM of oligonucleotide in the presence of 20 μg/ml DOTMA/DOPE solution for 4 hours at 37° C. The medium was replaced with methionine-free medium plus 10% dialyzed fetal calf serum and 1 μmM antisense oligonucleotide. The cells were incubated for 1 hour in methionine-free medium, then 100 μCi/ml ³⁵S-labeled methionine/cysteine mixture was added to the cells. Cells were incubated an additional 2 hours, washed 4 times with PBS, and extracted with buffer containing 20 mM Tris, pH 7.2, 20 mM KCl, 5 mM EDTA, 1% Triton X-100, 0.1 mM leupeptin, 10 μg/ml aprotinin, and 1 mM PMSF. ICAM-1 was immunoprecipitated from the extracts by incubating with a murine-specific ICAM-1 antibody (YN1/1.7.4) followed by protein G-sepharose. The immunoprecipitates were analyzed by SDS-PAGE and autoradiographed. Phosphorothioate oligonucleotides ISIS 3066 and 3069, which target the AUG codon of mouse ICAM-1, inhibited ICAM-1 synthesis by 48% and 63%, respectively, while oligonucleotides ISIS 3065 and ISIS 3082, which target sequences in the 3'-untranslated region of murine ICAM-1 mRNA inhibited ICAM-1 synthesis by 47% and 97%, respectively. The most active antisense oligonucleotide against mouse ICAM-1 was targeted to the 3'-untranslated region. ISIS 3082 was evaluated further based on these results; this 20-mer phosphorothioate oligonucleotide comprises the sequence (5' to 3') TGC ATC CCC CAG GCC ACC AT (SEQ ID NO: 83).

Example 20

Antisense Oligonucleotides to ICAM-1 Reduce Inflammatory Bowel Disease in Murine Model System A mouse model for inflammatory bowel disease (IBD) has recently been developed. Okayasu et al., *Gastroenterology* 1990, 98, 694–702. Administration of dextran sulfate to mice induces colitis that mimics human IBD in almost every detail. Dextran sulfate-induced IBD and human IBD have subsequently been closely compared at the histological level and the mouse model has been found to be an extremely reproducible and reliable model. It is used here to test the effect of ISIS 3082, a 20-base phosphorothioate antisense oligonucleotide which is complementary to the 3' untranslated region of the murine ICAM-1.

Female Swiss Webster mice (8 weeks of age) weighing approximately 25 to 30 grams are kept under standard conditions. Mice are allowed to acclimate for at least 5 days before initiation of experimental procedures. Mice are given 5% dextran sulfate sodium in their drinking water (available ad libitum) for 5 days. Concomitantly, ISIS 3082 oligonucleotide in pharmaceutical carrier, carrier alone (negative control) or TGF-β (known to protect against dextran sulfate-mediated colitis in mice) is administered. ISIS 3082 was given as daily subcutaneous injection of 1 mg/kg or 10 mg/kg for 5 days. TGF-β was given as 1 μg/mouse intracolonically. At 1 mg/kg, the oligonucleotide was as effective as TGF-β in protecting against dextran-sulfate-induced colitis.

Figure 16:
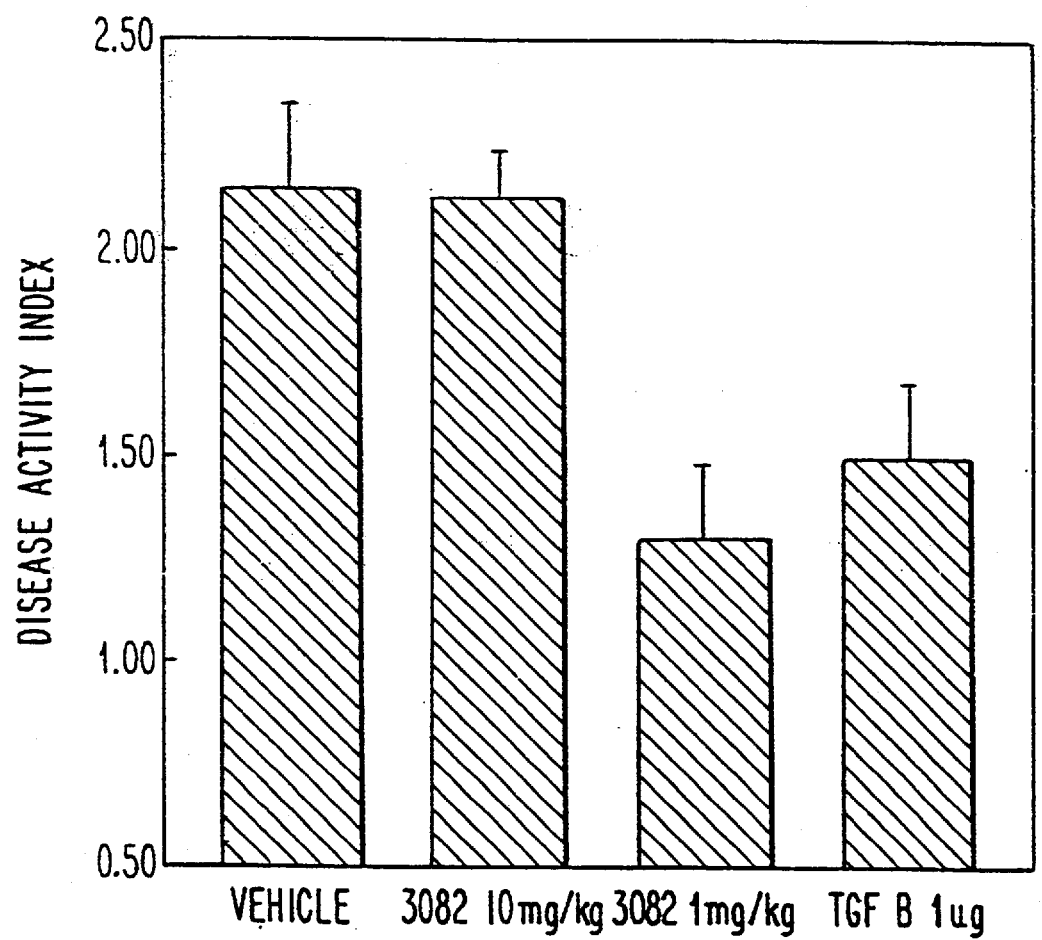
FIG. 16 is a bar graph showing the effect of ISIS 3082 on dextran sulfate (DSS)-induced inflammatory bowel disease.

Mice were sacrificed on day 6 and colons were subjected to histopathologic evaluation. Until sacrifice, disease activity was monitored by observing mice for weight changes and by observing stools for evidence of colitis. Mice were weighed daily. Stools were observed daily for changes in consistency and for presence of occult or gross bleeding. A scoring system was used to develop a disease activity index by which weight loss, stool consistency and presence of bleeding were graded on a scale of 0 to 3 (0 being normal and 3 being most severely affected) and an index was calculated. Drug-induced changes in the disease activity index were analyzed statistically. The disease activity index has been shown to correlate extremely well with IRD in general. Results are shown in FIG. 16. At 1 mg/kg, the oligonucleotide reduced the disease index by 40%.

Example 21

Antisense Oligonucleotide to ICAM-1 Increases Survival in Murine Heterotopic Heart Transplant Model To determine the therapeutic effects of ICAM-1 antisense oligonucleotide in preventing allograft rejection the murine ICAM-1 specific oligonucleotide ISIS 3082 was tested for activity in a murine vascularized heterotopic heart transplant model. Hearts from Balb/c mice were transplanted into the abdominal cavity of C3H mice as primary vascularized grafts essentially as described by Isobe et al., *Circulation* 1991, 84, 1246–1255. Oligonucleotides were administered by continuous intravenous administration via a 7-day Alzet pump. The mean survival time for untreated mice was 9.2±0.8 days (8, 9, 9, 9, 10, 10 days). Treatment of the mice for 7 days with 5 mg/kg ISIS 3082 increased the mean survival time to 14.3±4.6 days (11, 12, 13, 21 days).

Example 22

Antisense Oligonucleotide to ICAM-1 Decreases Leukocyte Migration

Leukocyte infiltration of tissues and organs is a major aspect of the inflammatory process and contributes to tissue damage resulting from inflammation. The effect of ISIS 3082 on leukocyte migration was examined using a mouse model in which carrageenan-soaked sponges were implanted subcutaneously. Carrageenan stimulates leukocyte migration and edema. Effect of oligonucleotide on leukocyte migration in inflammatory exudates is evaluated by quantitation of leukocytes infiltrating the implanted sponges. Following a four hour fast, 40 mice were assigned randomly to eight groups each containing five mice. Each mouse was anesthetized with Metofane® and a polyester sponge impregnated with 1 ml of a 20 mg/ml solution of carrageenan was implanted subcutaneously. Saline was administered intravenously to Group 1 at 10 ml/kg four hours prior to sponge implantation and this served as the vehicle control. Indomethacin (positive control) was administered orally at 3 mg/kg at a volume of 20 ml/kg to Group 2 immediately following surgery, again 6–8 hours later and again at 21 hours post-implantation. ISIS 3082 was administered intravenously at 5 mg/kg to Group 3 four hours prior to sponge implantation. ISIS 3082 was administered intravenously at 5 mg/kg to Group 4 immediately following sponge implantation. ISIS 3082 was administered intravenously at 5 mg/kg to Groups 5, 6, 7 and 8 at 2, 4, 8 and 18 hours following sponge implantation, respectively. Twenty-four hours after implantation, sponges were removed, immersed in EDTA and saline (5 ml) and squeezed dry. Total numbers of leukocytes in sponge exudate mixtures were determined.

The oral administration of indomethacin at 3 mg/kg produced a 79% reduction in mean leukocyte count when compared to the vehicle control group.

A 42% reduction in mean leukocyte count was observed following the administration of ISIS 3082 at 5 mg/kg four hours prior to sponge implantation (Group 3). A 47% reduction in mean leukocyte count was observed following the administration of ISIS 3082 at 5 mg/kg immediately following sponge implantation (Group 4). All animals appeared normal throughout the course of study.

What is claimed is:

1. An antisense oligonucleotide targeted to a translation initiation site of a nucleic acid presented in FIG. 1 encoding intercellular adhesion molecule-1, said antisense oligonucleotide comprising from 8 to 25 nucleotide subunits, wherein said antisense oligonucleotide modulates the production of said intercellular adhesion molecule-1.

2. The antisense oligonucleotide of claim 1 comprising from 12 to 22 nucleotide subunits.

3. The antisense oligonucleotide of claim 1, said antisense oligonucieotide having from 12 to 22 nucleotide subunits comprising a sequence which hybridizes via Watson-Crick base-pairing with a sequence contained within the sequence 3'-GCCCCCGACGACCCTCGGTATCGCTCCGACTC CAACG-5' (SEQ ID NO:86) thereby modulating production of said intercellular adhesion molecule-1.

4. An antisense oligonucleotide up to 50 nucleic acid base units in length and comprising the sequence

| | |
|---|---|
| 5'-CGGGGGCTGCTGGGAGCCAT | SEQ ID NO:8, |
| 5'-TGGGAGCCATAGCGAGGC | SEQ ID NO:1, |
| 5'-TGGGAGCCATAGCGAG | SEQ ID NO:20, |
| 5'-GGAGCCATAGCGAGGC | SEQ ID NO:21, |
| 5'-AGCCATAGCGAGGC | SEQ ID NO:17, |
| 5'-CCATAGCGAGGC | SEQ ID NO:18, |
| 5'-CATAGCGAGGCTGAGGTTGC | SEQ ID NO:7, or |
| 5'-ATAGCGAGGC | SEQ ID NO:19. |

* * * * *